(12) United States Patent
White et al.

(10) Patent No.: US 8,858,561 B2
(45) Date of Patent: Oct. 14, 2014

(54) PATIENT-SPECIFIC ALIGNMENT GUIDE

(75) Inventors: John R. White, Winona Lake, IN (US); Kurt Schmidt, Warsaw, IN (US); Troy W. Hershberger, Winona Lake, IN (US); Thomas C. Raish, Warsaw, IN (US); Ryan J. Schoenefeld, Fort Wayne, IN (US); William J. Hamman, Winona Lake, IN (US); Jason D. Meridew, Warsaw, IN (US); Tyler D. Witt, Warsaw, IN (US); Robert Metzger, Wakarusa, IN (US); J. Scott Deming, Warsaw, IN (US); Tim Clijmans, Leuven (BE); Frederik Gelaude, Leuven (BE)

(73) Assignee: Biomet Manufacturing, LLC, Warsaw, IN (US)

( * ) Notice: Subject to any disclaimer, the term of this patent is extended or adjusted under 35 U.S.C. 154(b) by 302 days.

(21) Appl. No.: 12/486,992

(22) Filed: Jun. 18, 2009

(65) Prior Publication Data

US 2009/0254093 A1 Oct. 8, 2009

Related U.S. Application Data

(63) Continuation-in-part of application No. 12/039,849, filed on Feb. 29, 2008, now Pat. No. 8,282,646, and a continuation-in-part of application No. 11/756,057, filed on May 31, 2007, now Pat. No. 8,092,465, which is a continuation-in-part of application No. 12/025,414, filed on Feb. 4, 2008, now Pat. No. 8,298,237.

(60) Provisional application No. 60/892,349, filed on Mar. 1, 2007, provisional application No. 60/812,694, filed on Jun. 9, 2006, provisional application No. 60/953,637, filed on Aug. 2, 2007.

(51) Int. Cl.
| | |
|---|---|
| *A61F 2/46* | (2006.01) |
| *A61B 17/17* | (2006.01) |
| *A61B 17/56* | (2006.01) |
| *A61B 19/00* | (2006.01) |
| *A61B 17/00* | (2006.01) |

(52) U.S. Cl.
CPC ......... *A61B 17/175* (2013.01); *A61B 2017/568* (2013.01); *A61B 19/50* (2013.01); *A61B 2017/00526* (2013.01)
USPC .......................................... 606/86 R; 606/89

(58) Field of Classification Search
USPC ................................................ 606/86 R–89
See application file for complete search history.

(56) References Cited

U.S. PATENT DOCUMENTS

| | | | |
|---|---|---|---|
| 1,480,285 A | 1/1924 | Moore | |
| 2,181,746 A | 11/1939 | Siebrandt | |

(Continued)

FOREIGN PATENT DOCUMENTS

| | | | |
|---|---|---|---|
| CA | 2447694 A1 | 12/2002 | |
| CA | 2501041 A1 | 4/2004 | |

(Continued)

OTHER PUBLICATIONS

Great Britain Search Report mailed Dec. 18, 2006 for GB0619534.1 filed Oct. 3, 2006 of which PCT/GB2007/003737 filed Oct. 2, 2007 claims benefit; of which U.S. Appl. No. 12/444,143, filed Jul. 9, 2010 claims benefit.

(Continued)

*Primary Examiner* — Paul Prebilic
(74) *Attorney, Agent, or Firm* — Harness, Dickey

(57) ABSTRACT

An orthopedic apparatus includes an alignment guide attachable to one of a femoral joint surface of a femur of a patient. The alignment guide has a patient-specific three-dimensional engagement surface, and at least one guiding portion defining a guiding passage. The engagement surface anatomically matches a corresponding portion of the femoral joint surface.

9 Claims, 8 Drawing Sheets

(56) References Cited

U.S. PATENT DOCUMENTS

| | | | |
|---|---|---|---|
| 2,407,845 | A | 9/1946 | Nemeyer |
| 2,416,228 | A | 2/1947 | Sheppard |
| 2,618,913 | A | 11/1952 | Plancon et al. |
| 2,910,978 | A | 11/1959 | Urist |
| 3,840,904 | A | 10/1974 | Tronzo |
| 4,246,895 | A * | 1/1981 | Rehder ............ 606/89 |
| 4,306,866 | A | 12/1981 | Weissman |
| 4,324,006 | A | 4/1982 | Charnley |
| 4,421,112 | A | 12/1983 | Mains et al. |
| 4,436,684 | A | 3/1984 | White |
| 4,457,306 | A | 7/1984 | Borzone |
| 4,475,549 | A | 10/1984 | Oh |
| 4,506,393 | A | 3/1985 | Murphy |
| 4,524,766 | A | 6/1985 | Petersen |
| 4,528,980 | A | 7/1985 | Kenna |
| 4,619,658 | A | 10/1986 | Pappas et al. |
| 4,621,630 | A | 11/1986 | Kenna |
| 4,632,111 | A | 12/1986 | Roche |
| 4,633,862 | A * | 1/1987 | Petersen ............ 606/88 |
| 4,663,720 | A | 5/1987 | Duret et al. |
| 4,689,984 | A | 9/1987 | Kellner |
| 4,695,283 | A | 9/1987 | Aldinger |
| 4,696,292 | A | 9/1987 | Heiple |
| 4,703,751 | A | 11/1987 | Pohl |
| 4,704,686 | A | 11/1987 | Aldinger |
| 4,706,660 | A | 11/1987 | Petersen |
| 4,719,907 | A | 1/1988 | Banko et al. |
| 4,721,104 | A | 1/1988 | Kaufman et al. |
| 4,722,330 | A | 2/1988 | Russell et al. |
| 4,778,474 | A | 10/1988 | Homsy |
| 4,800,874 | A | 1/1989 | David et al. |
| 4,821,213 | A | 4/1989 | Cline et al. |
| 4,822,365 | A | 4/1989 | Walker et al. |
| 4,841,975 | A | 6/1989 | Woolson |
| 4,846,161 | A | 7/1989 | Roger |
| 4,871,975 | A | 10/1989 | Nawata et al. |
| 4,893,619 | A | 1/1990 | Dale et al. |
| 4,896,663 | A * | 1/1990 | Vandewalls ............ 606/79 |
| 4,927,422 | A | 5/1990 | Engelhardt |
| 4,936,862 | A | 6/1990 | Walker et al. |
| 4,952,213 | A | 8/1990 | Bowman et al. |
| 4,959,066 | A | 9/1990 | Dunn et al. |
| 4,976,737 | A | 12/1990 | Leake |
| 4,979,949 | A | 12/1990 | Matsen, III et al. |
| 4,985,037 | A | 1/1991 | Petersen |
| 5,002,579 | A | 3/1991 | Copf et al. |
| 5,007,936 | A | 4/1991 | Woolson |
| 5,030,221 | A | 7/1991 | Buechel et al. |
| 5,041,117 | A | 8/1991 | Engelhardt |
| 5,053,037 | A | 10/1991 | Lackey |
| 5,053,039 | A | 10/1991 | Hofmann et al. |
| 5,056,351 | A | 10/1991 | Stiver et al. |
| 5,086,401 | A | 2/1992 | Glassman et al. |
| 5,098,383 | A | 3/1992 | Hemmy et al. |
| 5,098,436 | A | 3/1992 | Ferrante et al. |
| 5,108,425 | A | 4/1992 | Hwang |
| 5,122,144 | A | 6/1992 | Bert et al. |
| 5,129,908 | A | 7/1992 | Petersen |
| 5,129,909 | A | 7/1992 | Sutherland |
| 5,133,760 | A | 7/1992 | Petersen et al. |
| 5,140,777 | A | 8/1992 | Ushiyama et al. |
| 5,150,304 | A | 9/1992 | Berchem et al. |
| 5,176,684 | A | 1/1993 | Ferrante et al. |
| 5,194,066 | A | 3/1993 | Van Zile |
| 5,246,444 | A | 9/1993 | Schreiber |
| 5,253,506 | A | 10/1993 | Davis et al. |
| 5,258,032 | A | 11/1993 | Bertin |
| 5,261,915 | A | 11/1993 | Durlacher et al. |
| 5,274,565 | A | 12/1993 | Reuben |
| 5,299,288 | A | 3/1994 | Glassman et al. |
| 5,300,077 | A | 4/1994 | Howell |
| 5,320,529 | A | 6/1994 | Pompa |
| 5,320,625 | A | 6/1994 | Bertin |
| 5,323,697 | A | 6/1994 | Schrock |
| 5,342,366 | A | 8/1994 | Whiteside et al. |
| 5,344,423 | A | 9/1994 | Dietz et al. |
| 5,360,446 | A | 11/1994 | Kennedy |
| 5,364,402 | A | 11/1994 | Mumme et al. |
| 5,368,858 | A | 11/1994 | Hunziker |
| 5,370,692 | A | 12/1994 | Fink et al. |
| 5,370,699 | A | 12/1994 | Hood et al. |
| 5,405,395 | A | 4/1995 | Coates |
| 5,408,409 | A | 4/1995 | Glassman et al. |
| 5,411,521 | A | 5/1995 | Putnam et al. |
| 5,415,662 | A | 5/1995 | Ferrante et al. |
| 5,417,694 | A | 5/1995 | Marik et al. |
| 5,438,263 | A | 8/1995 | Dworkin et al. |
| 5,440,496 | A | 8/1995 | Andersson et al. |
| 5,448,489 | A | 9/1995 | Reuben |
| 5,449,360 | A | 9/1995 | Schreiber |
| 5,452,407 | A | 9/1995 | Crook |
| 5,454,816 | A | 10/1995 | Ashby |
| 5,472,415 | A | 12/1995 | King et al. |
| 5,474,559 | A | 12/1995 | Bertin et al. |
| 5,490,854 | A | 2/1996 | Fisher et al. |
| 5,496,324 | A | 3/1996 | Barnes |
| 5,507,833 | A | 4/1996 | Bohn |
| 5,514,519 | A | 5/1996 | Neckers |
| 5,520,695 | A | 5/1996 | Luckman |
| 5,527,317 | A | 6/1996 | Ashby et al. |
| 5,539,649 | A | 7/1996 | Walsh et al. |
| 5,540,695 | A | 7/1996 | Levy |
| 5,545,222 | A | 8/1996 | Bonutti |
| 5,549,688 | A | 8/1996 | Ries et al. |
| 5,554,190 | A | 9/1996 | Draenert |
| 5,560,096 | A | 10/1996 | Stephens |
| 5,571,110 | A | 11/1996 | Matsen, III et al. |
| 5,578,037 | A | 11/1996 | Sanders et al. |
| 5,595,703 | A | 1/1997 | Swaelens et al. |
| 5,607,431 | A | 3/1997 | Dudasik et al. |
| 5,613,969 | A | 3/1997 | Jenkins, Jr. |
| 5,620,448 | A | 4/1997 | Puddu |
| 5,634,927 | A | 6/1997 | Houston et al. |
| 5,641,323 | A | 6/1997 | Caldarise |
| 5,658,294 | A | 8/1997 | Sederholm |
| 5,662,656 | A | 9/1997 | White |
| 5,662,710 | A | 9/1997 | Bonutti |
| 5,671,018 | A | 9/1997 | Ohara et al. |
| 5,677,107 | A | 10/1997 | Neckers |
| 5,681,354 | A | 10/1997 | Eckhoff |
| 5,682,886 | A | 11/1997 | Delp et al. |
| 5,683,469 | A | 11/1997 | Johnson et al. |
| 5,690,635 | A | 11/1997 | Matsen, III et al. |
| 5,697,933 | A | 12/1997 | Gundlapalli et al. |
| 5,702,460 | A | 12/1997 | Carls et al. |
| 5,702,464 | A | 12/1997 | Lackey et al. |
| 5,704,941 | A | 1/1998 | Jacober et al. |
| 5,722,978 | A * | 3/1998 | Jenkins, Jr. ............ 606/87 |
| 5,725,376 | A | 3/1998 | Poirier |
| 5,725,593 | A | 3/1998 | Caracciolo |
| 5,735,277 | A | 4/1998 | Schuster |
| 5,748,767 | A | 5/1998 | Raab |
| 5,749,875 | A | 5/1998 | Puddu |
| 5,749,876 | A | 5/1998 | Duvillier et al. |
| 5,762,125 | A | 6/1998 | Mastrorio |
| 5,768,134 | A | 6/1998 | Swaelens et al. |
| 5,769,092 | A | 6/1998 | Williamson, Jr. |
| 5,776,200 | A | 7/1998 | Johnson et al. |
| 5,786,217 | A | 7/1998 | Tubo et al. |
| 5,792,143 | A | 8/1998 | Samuelson et al. |
| 5,798,924 | A | 8/1998 | Eufinger et al. |
| 5,799,055 | A | 8/1998 | Peshkin et al. |
| 5,860,980 | A | 1/1999 | Axelson, Jr. et al. |
| 5,860,981 | A | 1/1999 | Bertin et al. |
| 5,871,018 | A | 2/1999 | Delp et al. |
| 5,876,456 | A | 3/1999 | Sederholm et al. |
| 5,879,398 | A | 3/1999 | Swarts et al. |
| 5,879,402 | A | 3/1999 | Lawes et al. |
| 5,880,976 | A | 3/1999 | DiGioia, III et al. |
| 5,885,297 | A | 3/1999 | Matsen, III |
| 5,885,298 | A | 3/1999 | Herrington et al. |
| 5,888,219 | A | 3/1999 | Bonutti |
| 5,895,389 | A | 4/1999 | Schenk et al. |
| 5,899,907 | A | 5/1999 | Johnson |

(56) References Cited

U.S. PATENT DOCUMENTS

| | | |
|---|---|---|
| 5,901,060 A | 5/1999 | Schall et al. |
| 5,911,724 A | 6/1999 | Wehrli |
| 5,921,988 A | 7/1999 | Legrand |
| 5,925,049 A | 7/1999 | Gustilo et al. |
| 5,942,370 A | 8/1999 | Neckers |
| 5,967,777 A | 10/1999 | Klein et al. |
| 5,976,149 A | 11/1999 | Masini |
| 5,980,526 A | 11/1999 | Johnson et al. |
| 6,033,415 A | 3/2000 | Mittelstadt et al. |
| 6,042,612 A * | 3/2000 | Voydeville ................. 623/23.15 |
| 6,056,754 A | 5/2000 | Haines et al. |
| 6,059,789 A | 5/2000 | Dinger et al. |
| 6,059,833 A | 5/2000 | Doets |
| 6,086,593 A | 7/2000 | Bonutti |
| 6,120,510 A | 9/2000 | Albrektsson et al. |
| 6,120,544 A | 9/2000 | Grundei et al. |
| 6,126,690 A | 10/2000 | Ateshian et al. |
| 6,126,692 A | 10/2000 | Robie et al. |
| 6,136,033 A | 10/2000 | Suemer |
| 6,156,069 A | 12/2000 | Amstutz |
| 6,159,217 A | 12/2000 | Robie et al. |
| 6,161,080 A | 12/2000 | Aouni-Ateshian et al. |
| 6,162,257 A | 12/2000 | Gustilo et al. |
| 6,187,010 B1 | 2/2001 | Masini |
| 6,195,615 B1 | 2/2001 | Lysen |
| 6,203,546 B1 | 3/2001 | MacMahon |
| 6,205,411 B1 | 3/2001 | DiGioia, III et al. |
| 6,206,927 B1 | 3/2001 | Fell et al. |
| 6,238,435 B1 | 5/2001 | Meulink et al. |
| 6,254,604 B1 | 7/2001 | Howell |
| 6,258,097 B1 | 7/2001 | Cook et al. |
| 6,264,698 B1 | 7/2001 | Lawes et al. |
| 6,270,529 B1 | 8/2001 | Terrill-Grisoni et al. |
| 6,273,891 B1 | 8/2001 | Masini |
| 6,290,727 B1 | 9/2001 | Otto et al. |
| 6,293,971 B1 | 9/2001 | Nelson et al. |
| 6,310,269 B1 | 10/2001 | Friese et al. |
| 6,312,258 B1 | 11/2001 | Ashman |
| 6,312,473 B1 | 11/2001 | Oshida |
| 6,319,285 B1 | 11/2001 | Chamier et al. |
| 6,325,829 B1 | 12/2001 | Schmotzer |
| 6,338,738 B1 | 1/2002 | Bellotti et al. |
| 6,343,987 B2 | 2/2002 | Hayama et al. |
| 6,354,011 B1 | 3/2002 | Albrecht |
| 6,361,563 B2 | 3/2002 | Terrill-Grisoni et al. |
| 6,379,299 B1 | 4/2002 | Borodulin et al. |
| 6,379,388 B1 | 4/2002 | Ensign et al. |
| 6,383,228 B1 | 5/2002 | Schmotzer |
| 6,391,251 B1 | 5/2002 | Keicher et al. |
| 6,395,005 B1 | 5/2002 | Lovell |
| 6,424,332 B1 | 7/2002 | Powell |
| 6,427,698 B1 | 8/2002 | Yoon |
| 6,459,948 B1 | 10/2002 | Ateshian et al. |
| 6,463,351 B1 | 10/2002 | Clynch |
| 6,475,243 B1 | 11/2002 | Sheldon et al. |
| 6,482,236 B2 | 11/2002 | Habecker |
| 6,488,715 B1 | 12/2002 | Pope et al. |
| 6,503,255 B1 | 1/2003 | Albrektsson et al. |
| 6,510,334 B1 | 1/2003 | Schuster et al. |
| 6,514,259 B2 | 2/2003 | Picard et al. |
| 6,517,583 B1 | 2/2003 | Pope et al. |
| 6,519,998 B2 | 2/2003 | Ertl et al. |
| 6,520,964 B2 | 2/2003 | Tallarida et al. |
| 6,533,737 B1 | 3/2003 | Brosseau et al. |
| 6,547,823 B2 | 4/2003 | Scarborough et al. |
| 6,554,837 B1 | 4/2003 | Hauri et al. |
| 6,556,008 B2 | 4/2003 | Thesen |
| 6,558,391 B2 | 5/2003 | Axelson, Jr. et al. |
| 6,558,428 B2 | 5/2003 | Park |
| 6,564,085 B2 | 5/2003 | Meaney et al. |
| 6,567,681 B1 | 5/2003 | Lindequist |
| 6,575,980 B1 | 6/2003 | Robie et al. |
| 6,575,982 B1 | 6/2003 | Bonutti |
| 6,591,581 B2 | 7/2003 | Schmieding |
| 6,605,293 B1 | 8/2003 | Giordano et al. |
| 6,622,567 B1 | 9/2003 | Hamel et al. |
| 6,629,999 B1 | 10/2003 | Serafin, Jr. |
| 6,641,617 B1 | 11/2003 | Merrill et al. |
| 6,682,566 B2 | 1/2004 | Draenert |
| 6,696,073 B2 | 2/2004 | Boyce et al. |
| 6,697,664 B2 | 2/2004 | Kienzle III et al. |
| 6,701,174 B1 | 3/2004 | Krause et al. |
| 6,709,462 B2 | 3/2004 | Hanssen |
| 6,711,431 B2 | 3/2004 | Sarin et al. |
| 6,711,432 B1 | 3/2004 | Krause et al. |
| 6,712,856 B1 | 3/2004 | Carignan et al. |
| 6,716,249 B2 | 4/2004 | Hyde |
| 6,725,077 B1 | 4/2004 | Balloni et al. |
| 6,738,657 B1 | 5/2004 | Franklin et al. |
| 6,740,092 B2 | 5/2004 | Lombardo et al. |
| 6,749,638 B1 | 6/2004 | Saladino |
| 6,750,653 B1 | 6/2004 | Zou et al. |
| 6,772,026 B2 | 8/2004 | Bradbury et al. |
| 6,780,190 B2 | 8/2004 | Maroney |
| 6,786,930 B2 | 9/2004 | Biscup |
| 6,799,066 B2 | 9/2004 | Steines et al. |
| 6,823,871 B2 | 11/2004 | Schmieding |
| 6,827,723 B2 | 12/2004 | Carson |
| 6,887,247 B1 | 5/2005 | Couture et al. |
| 6,905,514 B2 | 6/2005 | Carignan et al. |
| 6,923,817 B2 | 8/2005 | Carson et al. |
| 6,923,831 B2 | 8/2005 | Fell et al. |
| 6,932,842 B1 | 8/2005 | Litschko et al. |
| 6,942,475 B2 | 9/2005 | Ensign et al. |
| 6,944,518 B2 | 9/2005 | Roose |
| 6,945,976 B2 | 9/2005 | Ball et al. |
| 6,953,480 B2 | 10/2005 | Mears et al. |
| 6,960,216 B2 * | 11/2005 | Kolb et al. ....................... 606/96 |
| 6,990,220 B2 | 1/2006 | Ellis et al. |
| 7,029,479 B2 | 4/2006 | Tallarida et al. |
| 7,042,222 B2 | 5/2006 | Zheng et al. |
| 7,048,741 B2 | 5/2006 | Swanson |
| 7,050,877 B2 | 5/2006 | Iseki et al. |
| 7,060,074 B2 | 6/2006 | Rosa et al. |
| 7,074,241 B2 | 7/2006 | McKinnon |
| RE39,301 E | 9/2006 | Bertin |
| 7,104,997 B2 | 9/2006 | Lionberger et al. |
| 7,105,026 B2 | 9/2006 | Johnson et al. |
| 7,115,131 B2 | 10/2006 | Engh et al. |
| 7,121,832 B2 | 10/2006 | Hsieh et al. |
| 7,141,053 B2 | 11/2006 | Rosa et al. |
| D533,664 S | 12/2006 | Buttler et al. |
| 7,169,185 B2 | 1/2007 | Sidebotham |
| 7,176,466 B2 | 2/2007 | Rousso et al. |
| 7,184,814 B2 | 2/2007 | Lang et al. |
| 7,198,628 B2 | 4/2007 | Ondrla et al. |
| 7,218,232 B2 | 5/2007 | DiSilvestro et al. |
| 7,239,908 B1 | 7/2007 | Alexander et al. |
| 7,241,315 B2 | 7/2007 | Evans |
| 7,255,702 B2 | 8/2007 | Serra et al. |
| 7,258,701 B2 | 8/2007 | Aram et al. |
| 7,275,218 B2 | 9/2007 | Petrella et al. |
| 7,282,054 B2 | 10/2007 | Steffensmeier et al. |
| 7,294,133 B2 | 11/2007 | Zink et al. |
| 7,297,164 B2 | 11/2007 | Johnson et al. |
| 7,309,339 B2 | 12/2007 | Cusick et al. |
| 7,333,013 B2 | 2/2008 | Berger |
| 7,335,231 B2 | 2/2008 | McLean |
| 7,371,260 B2 | 5/2008 | Malinin |
| 7,383,164 B2 | 6/2008 | Aram et al. |
| 7,385,498 B2 | 6/2008 | Dobosz |
| 7,388,972 B2 | 6/2008 | Kitson |
| 7,390,327 B2 | 6/2008 | Collazo et al. |
| 7,392,076 B2 | 6/2008 | Moctezuma de La Barrera |
| 7,427,200 B2 | 9/2008 | Noble et al. |
| 7,427,272 B2 | 9/2008 | Richard et al. |
| 7,468,075 B2 | 12/2008 | Lang et al. |
| 7,474,223 B2 | 1/2009 | Nycz et al. |
| 7,488,325 B2 | 2/2009 | Qian |
| 7,494,510 B2 | 2/2009 | Zweymuller |
| 7,517,365 B2 | 4/2009 | Carignan et al. |
| 7,527,631 B2 | 5/2009 | Maroney et al. |
| 7,534,263 B2 | 5/2009 | Burdulis, Jr. et al. |
| 7,542,791 B2 | 6/2009 | Mire et al. |

(56) References Cited

U.S. PATENT DOCUMENTS

| | | |
|---|---|---|
| 7,559,931 B2 | 7/2009 | Stone |
| 7,575,602 B2 | 8/2009 | Amirouche et al. |
| 7,578,851 B2 | 8/2009 | Dong et al. |
| 7,582,091 B2 | 9/2009 | Duncan et al. |
| 7,591,821 B2 | 9/2009 | Kelman |
| 7,601,155 B2 | 10/2009 | Petersen |
| 7,604,639 B2 | 10/2009 | Swanson |
| 7,611,516 B2 | 11/2009 | Maroney |
| 7,618,451 B2 | 11/2009 | Berez et al. |
| 7,621,915 B2 | 11/2009 | Frederick et al. |
| 7,625,409 B2 | 12/2009 | Saltzman et al. |
| 7,646,161 B2 | 1/2010 | Albu-Schaffer et al. |
| 7,651,501 B2 | 1/2010 | Penenberg et al. |
| 7,670,345 B2 | 3/2010 | Plassky et al. |
| 7,682,398 B2 | 3/2010 | Croxton et al. |
| 7,695,477 B2 | 4/2010 | Creger et al. |
| 7,695,521 B2 | 4/2010 | Ely et al. |
| 7,699,847 B2 * | 4/2010 | Sheldon et al. .................. 606/53 |
| 7,704,253 B2 | 4/2010 | Bastian et al. |
| 7,723,395 B2 | 5/2010 | Ringeisen et al. |
| 7,780,672 B2 | 8/2010 | Metzger et al. |
| 7,780,740 B2 | 8/2010 | Steinberg |
| 7,794,466 B2 | 9/2010 | Merchant et al. |
| 7,794,467 B2 | 9/2010 | McGinley et al. |
| 7,794,504 B2 | 9/2010 | Case |
| 7,806,896 B1 | 10/2010 | Bonutti |
| 7,809,184 B2 | 10/2010 | Neubauer et al. |
| 7,819,925 B2 | 10/2010 | King et al. |
| 7,828,806 B2 | 11/2010 | Graf et al. |
| 7,850,698 B2 | 12/2010 | Straszheim-Morley et al. |
| 7,879,109 B2 | 2/2011 | Borden et al. |
| 7,892,261 B2 | 2/2011 | Bonutti |
| 7,896,921 B2 | 3/2011 | Smith et al. |
| 7,935,119 B2 | 5/2011 | Ammann et al. |
| 7,935,150 B2 | 5/2011 | Carignan et al. |
| 7,938,861 B2 | 5/2011 | King et al. |
| 7,959,637 B2 | 6/2011 | Fox et al. |
| 7,962,196 B2 | 6/2011 | Tuma |
| 7,963,968 B2 | 6/2011 | Dees, Jr. |
| 7,967,823 B2 | 6/2011 | Ammann et al. |
| 7,967,868 B2 | 6/2011 | White et al. |
| 7,974,677 B2 | 7/2011 | Mire et al. |
| 7,981,158 B2 | 7/2011 | Fitz et al. |
| 7,993,353 B2 | 8/2011 | Rossner et al. |
| 8,062,301 B2 | 11/2011 | Ammann et al. |
| 8,070,752 B2 | 12/2011 | Metzger et al. |
| 8,083,745 B2 | 12/2011 | Lang et al. |
| 8,083,746 B2 | 12/2011 | Novak |
| 8,083,749 B2 | 12/2011 | Taber |
| 8,086,336 B2 | 12/2011 | Christensen |
| 8,092,465 B2 | 1/2012 | Metzger et al. |
| 8,133,230 B2 | 3/2012 | Stevens et al. |
| 8,133,234 B2 | 3/2012 | Meridew et al. |
| 8,137,406 B2 | 3/2012 | Novak et al. |
| 8,167,951 B2 | 5/2012 | Ammann et al. |
| 8,170,641 B2 | 5/2012 | Belcher |
| 8,182,489 B2 | 5/2012 | Horacek |
| 8,192,441 B2 | 6/2012 | Collazo |
| 8,192,495 B2 | 6/2012 | Simpson et al. |
| 8,211,112 B2 | 7/2012 | Novak et al. |
| 8,241,292 B2 | 8/2012 | Collazo |
| 8,241,293 B2 | 8/2012 | Stone et al. |
| 8,265,790 B2 | 9/2012 | Amiot et al. |
| D669,176 S | 10/2012 | Frey |
| 8,282,646 B2 | 10/2012 | Schoenefeld et al. |
| 8,298,237 B2 | 10/2012 | Schoenefeld et al. |
| 8,303,596 B2 | 11/2012 | Plaβky et al. |
| D672,038 S | 12/2012 | Frey |
| 8,333,772 B2 | 12/2012 | Fox et al. |
| 8,355,773 B2 | 1/2013 | Leitner et al. |
| 8,377,066 B2 | 2/2013 | Katrana et al. |
| 8,398,646 B2 | 3/2013 | Metzger et al. |
| 8,407,067 B2 | 3/2013 | Uthgenannt et al. |
| 8,439,675 B2 | 5/2013 | De Moyer |
| 8,439,925 B2 | 5/2013 | Marino et al. |
| 8,469,961 B2 * | 6/2013 | Alleyne et al. .............. 606/86 R |
| 8,473,305 B2 | 6/2013 | Belcher et al. |
| 8,486,150 B2 | 7/2013 | White et al. |
| 8,532,807 B2 | 9/2013 | Metzger |
| 8,535,387 B2 | 9/2013 | Meridew et al. |
| 8,568,487 B2 | 10/2013 | Witt et al. |
| 8,591,516 B2 | 11/2013 | Metzger et al. |
| 8,597,365 B2 | 12/2013 | Meridew |
| 8,603,180 B2 | 12/2013 | White et al. |
| 8,608,749 B2 | 12/2013 | Meridew et al. |
| 8,632,547 B2 | 1/2014 | Maxson et al. |
| 2001/0005797 A1 | 6/2001 | Barlow et al. |
| 2001/0011190 A1 | 8/2001 | Park |
| 2001/0021876 A1 | 9/2001 | Terrill-Grisoni et al. |
| 2001/0054478 A1 | 12/2001 | Watanabe et al. |
| 2002/0007294 A1 | 1/2002 | Bradbury et al. |
| 2002/0029045 A1 | 3/2002 | Bonutti |
| 2002/0052606 A1 | 5/2002 | Bonutti |
| 2002/0059049 A1 | 5/2002 | Bradbury et al. |
| 2002/0082741 A1 | 6/2002 | Mazumder et al. |
| 2002/0087274 A1 | 7/2002 | Alexander et al. |
| 2002/0092532 A1 | 7/2002 | Yoon |
| 2002/0107522 A1 | 8/2002 | Picard et al. |
| 2002/0128872 A1 | 9/2002 | Giammattei |
| 2002/0147415 A1 | 10/2002 | Martelli |
| 2002/0193797 A1 | 12/2002 | Johnson et al. |
| 2003/0009171 A1 | 1/2003 | Tornier |
| 2003/0009234 A1 | 1/2003 | Treacy et al. |
| 2003/0011624 A1 | 1/2003 | Ellis |
| 2003/0018338 A1 | 1/2003 | Axelson et al. |
| 2003/0039676 A1 | 2/2003 | Boyce et al. |
| 2003/0055502 A1 | 3/2003 | Lang et al. |
| 2003/0105526 A1 | 6/2003 | Bryant et al. |
| 2003/0109784 A1 | 6/2003 | Loh et al. |
| 2003/0120276 A1 | 6/2003 | Tallarida et al. |
| 2003/0130741 A1 | 7/2003 | McMinn |
| 2003/0139817 A1 | 7/2003 | Tuke et al. |
| 2003/0158606 A1 | 8/2003 | Coon et al. |
| 2003/0171757 A1 | 9/2003 | Coon et al. |
| 2003/0216669 A1 | 11/2003 | Lang et al. |
| 2004/0018144 A1 | 1/2004 | Briscoe |
| 2004/0030245 A1 | 2/2004 | Noble et al. |
| 2004/0054372 A1 | 3/2004 | Corden et al. |
| 2004/0068187 A1 | 4/2004 | Krause et al. |
| 2004/0092932 A1 | 5/2004 | Aubin et al. |
| 2004/0098133 A1 | 5/2004 | Carignan et al. |
| 2004/0102852 A1 | 5/2004 | Johnson et al. |
| 2004/0102866 A1 | 5/2004 | Harris et al. |
| 2004/0106926 A1 | 6/2004 | Leitner et al. |
| 2004/0115586 A1 | 6/2004 | Andreiko et al. |
| 2004/0122439 A1 | 6/2004 | Dwyer et al. |
| 2004/0128026 A1 | 7/2004 | Harris et al. |
| 2004/0133276 A1 | 7/2004 | Lang et al. |
| 2004/0138754 A1 | 7/2004 | Lang et al. |
| 2004/0143336 A1 | 7/2004 | Burkinshaw |
| 2004/0147927 A1 | 7/2004 | Tsougarakis et al. |
| 2004/0148026 A1 | 7/2004 | Bonutti |
| 2004/0153079 A1 | 8/2004 | Tsougarakis et al. |
| 2004/0153087 A1 | 8/2004 | Sanford et al. |
| 2004/0158254 A1 | 8/2004 | Eisermann |
| 2004/0162619 A1 | 8/2004 | Blaylock et al. |
| 2004/0167390 A1 | 8/2004 | Alexander et al. |
| 2004/0171924 A1 | 9/2004 | Mire et al. |
| 2004/0172137 A1 | 9/2004 | Blaylock et al. |
| 2004/0181144 A1 | 9/2004 | Cinquin et al. |
| 2004/0204644 A1 | 10/2004 | Tsougarakis et al. |
| 2004/0204760 A1 | 10/2004 | Fitz et al. |
| 2004/0212586 A1 | 10/2004 | Denny |
| 2004/0220583 A1 | 11/2004 | Pieczynski et al. |
| 2004/0236341 A1 | 11/2004 | Petersen |
| 2004/0236424 A1 | 11/2004 | Berez et al. |
| 2004/0243481 A1 | 12/2004 | Bradbury et al. |
| 2004/0254584 A1 | 12/2004 | Sarin et al. |
| 2004/0260301 A1 | 12/2004 | Lionberger et al. |
| 2005/0008887 A1 | 1/2005 | Haymann et al. |
| 2005/0010227 A1 | 1/2005 | Paul |
| 2005/0010300 A1 | 1/2005 | Disilvestro et al. |
| 2005/0015022 A1 | 1/2005 | Richard et al. |
| 2005/0019664 A1 | 1/2005 | Matsumoto |

(56) References Cited

U.S. PATENT DOCUMENTS

| | | |
|---|---|---|
| 2005/0027303 A1 | 2/2005 | Lionberger et al. |
| 2005/0027361 A1 | 2/2005 | Reiley |
| 2005/0043806 A1 | 2/2005 | Cook et al. |
| 2005/0043837 A1 | 2/2005 | Rubbert et al. |
| 2005/0049524 A1 | 3/2005 | Lefevre et al. |
| 2005/0049603 A1 | 3/2005 | Calton et al. |
| 2005/0059873 A1 | 3/2005 | Glozman et al. |
| 2005/0060040 A1 | 3/2005 | Auxepaules et al. |
| 2005/0065628 A1 | 3/2005 | Roose |
| 2005/0070897 A1 | 3/2005 | Petersen |
| 2005/0071015 A1 | 3/2005 | Sekel |
| 2005/0075641 A1 | 4/2005 | Singhatat et al. |
| 2005/0096535 A1 | 5/2005 | de la Barrera |
| 2005/0113841 A1* | 5/2005 | Sheldon et al. ............... 606/88 |
| 2005/0113846 A1 | 5/2005 | Carson |
| 2005/0119664 A1 | 6/2005 | Carignan et al. |
| 2005/0131662 A1 | 6/2005 | Ascenzi et al. |
| 2005/0137708 A1 | 6/2005 | Clark |
| 2005/0148843 A1 | 7/2005 | Roose |
| 2005/0149042 A1 | 7/2005 | Metzger |
| 2005/0171545 A1 | 8/2005 | Walsh et al. |
| 2005/0177245 A1 | 8/2005 | Leatherbury et al. |
| 2005/0203536 A1 | 9/2005 | Laffargue et al. |
| 2005/0203540 A1 | 9/2005 | Broyles |
| 2005/0209597 A1 | 9/2005 | Long et al. |
| 2005/0216305 A1 | 9/2005 | Funderud |
| 2005/0222573 A1 | 10/2005 | Branch et al. |
| 2005/0228393 A1 | 10/2005 | Williams et al. |
| 2005/0234461 A1 | 10/2005 | Burdulis et al. |
| 2005/0234465 A1 | 10/2005 | McCombs et al. |
| 2005/0234468 A1 | 10/2005 | Carson |
| 2005/0240195 A1 | 10/2005 | Axelson et al. |
| 2005/0240267 A1 | 10/2005 | Randall et al. |
| 2005/0244239 A1 | 11/2005 | Shimp |
| 2005/0245934 A1 | 11/2005 | Tuke et al. |
| 2005/0245936 A1* | 11/2005 | Tuke et al. ............... 606/89 |
| 2005/0251147 A1 | 11/2005 | Novak |
| 2005/0267353 A1 | 12/2005 | Marquart et al. |
| 2005/0267485 A1 | 12/2005 | Cordes et al. |
| 2005/0267584 A1 | 12/2005 | Burdulis et al. |
| 2005/0273114 A1 | 12/2005 | Novak |
| 2005/0283252 A1 | 12/2005 | Coon et al. |
| 2005/0283253 A1 | 12/2005 | Coon et al. |
| 2006/0004284 A1 | 1/2006 | Grunschlager et al. |
| 2006/0015120 A1 | 1/2006 | Richard et al. |
| 2006/0030853 A1 | 2/2006 | Haines |
| 2006/0038520 A1 | 2/2006 | Negoro et al. |
| 2006/0052725 A1 | 3/2006 | Santilli |
| 2006/0058803 A1 | 3/2006 | Cuckler et al. |
| 2006/0058884 A1 | 3/2006 | Aram et al. |
| 2006/0058886 A1 | 3/2006 | Wozencroft |
| 2006/0089621 A1 | 4/2006 | Fard |
| 2006/0093988 A1 | 5/2006 | Swaelens et al. |
| 2006/0094951 A1 | 5/2006 | Dean et al. |
| 2006/0095044 A1 | 5/2006 | Grady et al. |
| 2006/0100832 A1 | 5/2006 | Bowman |
| 2006/0111722 A1 | 5/2006 | Bouadi |
| 2006/0122616 A1 | 6/2006 | Bennett et al. |
| 2006/0136058 A1 | 6/2006 | Pietrzak |
| 2006/0142657 A1 | 6/2006 | Quaid et al. |
| 2006/0149283 A1 | 7/2006 | May et al. |
| 2006/0155380 A1 | 7/2006 | Clemow et al. |
| 2006/0161167 A1 | 7/2006 | Myers et al. |
| 2006/0172263 A1 | 8/2006 | Quadling et al. |
| 2006/0178497 A1 | 8/2006 | Gevaert et al. |
| 2006/0184177 A1 | 8/2006 | Echeverri |
| 2006/0184250 A1 | 8/2006 | Bandoh et al. |
| 2006/0190086 A1 | 8/2006 | Clemow et al. |
| 2006/0192319 A1 | 8/2006 | Solar |
| 2006/0195111 A1 | 8/2006 | Couture |
| 2006/0195194 A1 | 8/2006 | Gunther |
| 2006/0195198 A1 | 8/2006 | James |
| 2006/0200158 A1 | 9/2006 | Farling et al. |
| 2006/0204932 A1 | 9/2006 | Haymann et al. |
| 2006/0210644 A1 | 9/2006 | Levin |
| 2006/0217808 A1 | 9/2006 | Novak et al. |
| 2006/0235421 A1 | 10/2006 | Rosa et al. |
| 2006/0241635 A1 | 10/2006 | Stumpo et al. |
| 2006/0241636 A1 | 10/2006 | Novak et al. |
| 2006/0271058 A1 | 11/2006 | Ashton et al. |
| 2006/0276796 A1 | 12/2006 | Creger et al. |
| 2006/0276797 A1 | 12/2006 | Botimer |
| 2006/0287733 A1 | 12/2006 | Bonutti |
| 2006/0293681 A1 | 12/2006 | Claypool et al. |
| 2007/0015995 A1 | 1/2007 | Lang et al. |
| 2007/0016209 A1 | 1/2007 | Ammann et al. |
| 2007/0027680 A1 | 2/2007 | Ashley et al. |
| 2007/0066917 A1 | 3/2007 | Hodorek et al. |
| 2007/0073137 A1 | 3/2007 | Schoenefeld |
| 2007/0083214 A1 | 4/2007 | Duncan et al. |
| 2007/0083266 A1 | 4/2007 | Lang |
| 2007/0100258 A1 | 5/2007 | Shoham et al. |
| 2007/0100450 A1 | 5/2007 | Hodorek |
| 2007/0100462 A1 | 5/2007 | Lang et al. |
| 2007/0118055 A1 | 5/2007 | McCombs |
| 2007/0118138 A1 | 5/2007 | Seo et al. |
| 2007/0118243 A1 | 5/2007 | Schroeder et al. |
| 2007/0150068 A1 | 6/2007 | Dong et al. |
| 2007/0156066 A1 | 7/2007 | McGinley et al. |
| 2007/0156171 A1 | 7/2007 | Lang et al. |
| 2007/0162038 A1* | 7/2007 | Tuke ............... 606/88 |
| 2007/0162039 A1 | 7/2007 | Wozencroft |
| 2007/0173946 A1 | 7/2007 | Bonutti |
| 2007/0173948 A1 | 7/2007 | Meridew et al. |
| 2007/0185498 A2 | 8/2007 | Lavallee |
| 2007/0191962 A1 | 8/2007 | Jones et al. |
| 2007/0198022 A1 | 8/2007 | Lang et al. |
| 2007/0203430 A1 | 8/2007 | Lang et al. |
| 2007/0203605 A1 | 8/2007 | Melton et al. |
| 2007/0219639 A1 | 9/2007 | Otto et al. |
| 2007/0219640 A1 | 9/2007 | Steinberg |
| 2007/0224238 A1 | 9/2007 | Mansmann et al. |
| 2007/0226986 A1 | 10/2007 | Park et al. |
| 2007/0233121 A1 | 10/2007 | Carson et al. |
| 2007/0233136 A1 | 10/2007 | Wozencroft |
| 2007/0233140 A1 | 10/2007 | Metzger et al. |
| 2007/0233141 A1 | 10/2007 | Park et al. |
| 2007/0233269 A1 | 10/2007 | Steines et al. |
| 2007/0233272 A1 | 10/2007 | Boyce et al. |
| 2007/0238069 A1 | 10/2007 | Lovald et al. |
| 2007/0239282 A1 | 10/2007 | Caylor et al. |
| 2007/0239481 A1 | 10/2007 | DiSilvestro et al. |
| 2007/0244487 A1 | 10/2007 | Ammann et al. |
| 2007/0250169 A1 | 10/2007 | Lang |
| 2007/0253617 A1 | 11/2007 | Arata et al. |
| 2007/0255288 A1 | 11/2007 | Mahfouz et al. |
| 2007/0255412 A1 | 11/2007 | Hajaj et al. |
| 2007/0262867 A1 | 11/2007 | Westrick et al. |
| 2007/0272747 A1 | 11/2007 | Woods et al. |
| 2007/0276224 A1 | 11/2007 | Lang et al. |
| 2007/0276400 A1 | 11/2007 | Moore et al. |
| 2007/0276501 A1 | 11/2007 | Betz et al. |
| 2007/0288029 A1 | 12/2007 | Justin et al. |
| 2007/0288030 A1 | 12/2007 | Metzger et al. |
| 2008/0009952 A1 | 1/2008 | Hodge |
| 2008/0015599 A1 | 1/2008 | D'Alessio et al. |
| 2008/0015603 A1 | 1/2008 | Collazo |
| 2008/0015604 A1 | 1/2008 | Collazo |
| 2008/0015605 A1 | 1/2008 | Collazo |
| 2008/0021299 A1 | 1/2008 | Meulink |
| 2008/0021494 A1 | 1/2008 | Schmelzeisen-Redeker et al. |
| 2008/0021567 A1 | 1/2008 | Meulink et al. |
| 2008/0027563 A1 | 1/2008 | Johnson et al. |
| 2008/0033442 A1* | 2/2008 | Amiot et al. ............... 606/80 |
| 2008/0039850 A1 | 2/2008 | Rowley et al. |
| 2008/0051799 A1 | 2/2008 | Bonutti |
| 2008/0051910 A1 | 2/2008 | Kammerzell et al. |
| 2008/0058945 A1 | 3/2008 | Hajaj et al. |
| 2008/0058947 A1 | 3/2008 | Earl et al. |
| 2008/0062183 A1 | 3/2008 | Swaelens |
| 2008/0065225 A1 | 3/2008 | Wasielewski et al. |
| 2008/0097451 A1 | 4/2008 | Chen et al. |
| 2008/0112996 A1 | 5/2008 | Harlow et al. |
| 2008/0114370 A1 | 5/2008 | Schoenefeld |

(56) References Cited

U.S. PATENT DOCUMENTS

| | | |
|---|---|---|
| 2008/0133022 A1 | 6/2008 | Caylor |
| 2008/0140081 A1 | 6/2008 | Heavener et al. |
| 2008/0140209 A1 | 6/2008 | Iannotti et al. |
| 2008/0140213 A1 | 6/2008 | Ammann et al. |
| 2008/0146969 A1 | 6/2008 | Kurtz |
| 2008/0147072 A1 | 6/2008 | Park et al. |
| 2008/0147073 A1 | 6/2008 | Ammann et al. |
| 2008/0161815 A1 | 7/2008 | Schoenefeld et al. |
| 2008/0161816 A1 | 7/2008 | Stevens et al. |
| 2008/0172125 A1 | 7/2008 | Ek |
| 2008/0195099 A1 | 8/2008 | Minas |
| 2008/0195107 A1 | 8/2008 | Cuckler et al. |
| 2008/0195108 A1 | 8/2008 | Bhatnagar et al. |
| 2008/0195109 A1 | 8/2008 | Hunter et al. |
| 2008/0195216 A1 | 8/2008 | Philipp |
| 2008/0200926 A1 | 8/2008 | Verard et al. |
| 2008/0208200 A1 | 8/2008 | Crofford |
| 2008/0208353 A1 | 8/2008 | Kumar et al. |
| 2008/0215059 A1 | 9/2008 | Carignan et al. |
| 2008/0230422 A1 | 9/2008 | Pleil et al. |
| 2008/0234664 A1 | 9/2008 | May et al. |
| 2008/0234683 A1 | 9/2008 | May |
| 2008/0234685 A1 | 9/2008 | Gjerde |
| 2008/0234833 A1 | 9/2008 | Bandoh et al. |
| 2008/0243127 A1 | 10/2008 | Lang et al. |
| 2008/0255674 A1 | 10/2008 | Rahaman et al. |
| 2008/0257363 A1 | 10/2008 | Schoenefeld et al. |
| 2008/0262500 A1 | 10/2008 | Collazo |
| 2008/0262624 A1 | 10/2008 | White et al. |
| 2008/0269906 A1 | 10/2008 | Iannotti et al. |
| 2008/0275452 A1 | 11/2008 | Lang et al. |
| 2008/0281328 A1 | 11/2008 | Lang et al. |
| 2008/0281329 A1 | 11/2008 | Fitz et al. |
| 2008/0281426 A1 | 11/2008 | Fitz et al. |
| 2008/0287926 A1 | 11/2008 | Abou El Kheir |
| 2008/0287954 A1 | 11/2008 | Kunz et al. |
| 2008/0294170 A1 | 11/2008 | O'Brien |
| 2008/0294266 A1 | 11/2008 | Steinberg |
| 2008/0300600 A1 | 12/2008 | Guelat et al. |
| 2008/0306485 A1 | 12/2008 | Coon et al. |
| 2008/0306558 A1 | 12/2008 | Hakki |
| 2008/0312659 A1 | 12/2008 | Metzger et al. |
| 2008/0319448 A1 | 12/2008 | Lavallee et al. |
| 2009/0012526 A1 | 1/2009 | Fletcher |
| 2009/0018546 A1 | 1/2009 | Daley |
| 2009/0018666 A1 | 1/2009 | Grundei et al. |
| 2009/0024131 A1 | 1/2009 | Metzger et al. |
| 2009/0024169 A1 | 1/2009 | Triplett et al. |
| 2009/0043556 A1 | 2/2009 | Axelson et al. |
| 2009/0076371 A1 | 3/2009 | Lang et al. |
| 2009/0076512 A1 | 3/2009 | Ammann et al. |
| 2009/0076520 A1 | 3/2009 | Choi |
| 2009/0076555 A1 | 3/2009 | Lowry et al. |
| 2009/0082770 A1 | 3/2009 | Worner et al. |
| 2009/0082774 A1 | 3/2009 | Oti et al. |
| 2009/0087276 A1 | 4/2009 | Rose |
| 2009/0088674 A1 | 4/2009 | Caillouette et al. |
| 2009/0088753 A1 | 4/2009 | Aram et al. |
| 2009/0088754 A1 | 4/2009 | Aker et al. |
| 2009/0088755 A1 | 4/2009 | Aker et al. |
| 2009/0088758 A1 | 4/2009 | Bennett |
| 2009/0088759 A1 | 4/2009 | Aram et al. |
| 2009/0088760 A1 | 4/2009 | Aram et al. |
| 2009/0088761 A1 | 4/2009 | Roose et al. |
| 2009/0088762 A1 | 4/2009 | Koenemann |
| 2009/0088763 A1 | 4/2009 | Aram et al. |
| 2009/0088865 A1 | 4/2009 | Brehm |
| 2009/0088866 A1 | 4/2009 | Case |
| 2009/0089034 A1 | 4/2009 | Penney et al. |
| 2009/0089081 A1 | 4/2009 | Haddad |
| 2009/0093815 A1 | 4/2009 | Fletcher et al. |
| 2009/0093816 A1 | 4/2009 | Roose et al. |
| 2009/0096613 A1 | 4/2009 | Westrick |
| 2009/0099567 A1 | 4/2009 | Zajac |
| 2009/0105837 A1 | 4/2009 | Lafosse et al. |
| 2009/0118736 A1 | 5/2009 | Kreuzer |
| 2009/0118769 A1 | 5/2009 | Sixto, Jr. et al. |
| 2009/0131941 A1 | 5/2009 | Park et al. |
| 2009/0131942 A1 | 5/2009 | Aker et al. |
| 2009/0138020 A1 | 5/2009 | Park et al. |
| 2009/0149964 A1 | 6/2009 | May et al. |
| 2009/0149965 A1 | 6/2009 | Quaid |
| 2009/0149977 A1 | 6/2009 | Schendel |
| 2009/0151736 A1 | 6/2009 | Belcher et al. |
| 2009/0157083 A1 | 6/2009 | Park et al. |
| 2009/0163922 A1 | 6/2009 | Meridew et al. |
| 2009/0163923 A1 | 6/2009 | Flett et al. |
| 2009/0164024 A1 | 6/2009 | Rudan et al. |
| 2009/0177282 A1 | 7/2009 | Bureau et al. |
| 2009/0187193 A1 | 7/2009 | Maroney et al. |
| 2009/0209884 A1 | 8/2009 | Van Vorhis et al. |
| 2009/0209961 A1 | 8/2009 | Ferrante et al. |
| 2009/0222014 A1 | 9/2009 | Bojarski et al. |
| 2009/0222015 A1 | 9/2009 | Park et al. |
| 2009/0222016 A1 | 9/2009 | Park et al. |
| 2009/0222103 A1 | 9/2009 | Fitz et al. |
| 2009/0226068 A1 | 9/2009 | Fitz et al. |
| 2009/0228016 A1 | 9/2009 | Alvarez |
| 2009/0234360 A1 | 9/2009 | Alexander |
| 2009/0248044 A1 | 10/2009 | Amiot et al. |
| 2009/0250413 A1 | 10/2009 | Hoeppner |
| 2009/0254367 A1 | 10/2009 | Belcher et al. |
| 2009/0259312 A1 | 10/2009 | Shterling et al. |
| 2009/0270868 A1 | 10/2009 | Park et al. |
| 2009/0274350 A1 | 11/2009 | Pavlovskaia et al. |
| 2009/0287217 A1 | 11/2009 | Ammann et al. |
| 2009/0306676 A1 | 12/2009 | Lang et al. |
| 2009/0307893 A1 | 12/2009 | Burdulis, Jr. et al. |
| 2009/0318836 A1 | 12/2009 | Stone et al. |
| 2009/0318921 A1 | 12/2009 | White et al. |
| 2010/0010493 A1* | 1/2010 | Dower ............................. 606/87 |
| 2010/0016984 A1 | 1/2010 | Trabish |
| 2010/0016986 A1 | 1/2010 | Trabish |
| 2010/0023015 A1 | 1/2010 | Park |
| 2010/0030231 A1 | 2/2010 | Revie et al. |
| 2010/0036404 A1 | 2/2010 | Yi et al. |
| 2010/0042105 A1 | 2/2010 | Park et al. |
| 2010/0049195 A1 | 2/2010 | Park et al. |
| 2010/0057088 A1* | 3/2010 | Shah ............................... 606/88 |
| 2010/0076439 A1 | 3/2010 | Hatch |
| 2010/0076505 A1 | 3/2010 | Borja |
| 2010/0076563 A1 | 3/2010 | Otto et al. |
| 2010/0076571 A1 | 3/2010 | Hatch |
| 2010/0082034 A1 | 4/2010 | Remia |
| 2010/0082035 A1 | 4/2010 | Keefer |
| 2010/0087829 A1 | 4/2010 | Metzger et al. |
| 2010/0094295 A1 | 4/2010 | Schnieders et al. |
| 2010/0105011 A1 | 4/2010 | Karkar et al. |
| 2010/0121334 A1* | 5/2010 | Couture et al. ................. 606/87 |
| 2010/0121335 A1 | 5/2010 | Penenberg et al. |
| 2010/0137869 A1 | 6/2010 | Borja et al. |
| 2010/0137924 A1 | 6/2010 | Tuke et al. |
| 2010/0145343 A1 | 6/2010 | Johnson et al. |
| 2010/0145344 A1 | 6/2010 | Jordan et al. |
| 2010/0152782 A1 | 6/2010 | Stone et al. |
| 2010/0160917 A1 | 6/2010 | Fitz et al. |
| 2010/0168752 A1* | 7/2010 | Edwards ......................... 606/87 |
| 2010/0168754 A1 | 7/2010 | Fitz et al. |
| 2010/0168857 A1 | 7/2010 | Hatch |
| 2010/0179663 A1 | 7/2010 | Steinberg |
| 2010/0185202 A1 | 7/2010 | Lester et al. |
| 2010/0191244 A1 | 7/2010 | White et al. |
| 2010/0198224 A1* | 8/2010 | Metzger et al. ................. 606/87 |
| 2010/0212138 A1 | 8/2010 | Carroll et al. |
| 2010/0217109 A1 | 8/2010 | Belcher |
| 2010/0217270 A1 | 8/2010 | Polinski et al. |
| 2010/0217336 A1 | 8/2010 | Crawford et al. |
| 2010/0217338 A1 | 8/2010 | Carroll et al. |
| 2010/0228257 A1 | 9/2010 | Bonutti |
| 2010/0249657 A1 | 9/2010 | Nycz et al. |
| 2010/0249796 A1 | 9/2010 | Nycz |
| 2010/0256649 A1 | 10/2010 | Capsal et al. |
| 2010/0262150 A1 | 10/2010 | Lian |
| 2010/0274253 A1 | 10/2010 | Ure |
| 2010/0281678 A1 | 11/2010 | Burdulis, Jr. et al. |

(56) References Cited

U.S. PATENT DOCUMENTS

| | | |
|---|---|---|
| 2010/0286700 A1 | 11/2010 | Snider et al. |
| 2010/0292743 A1 | 11/2010 | Singhal et al. |
| 2010/0305574 A1 | 12/2010 | Fitz et al. |
| 2010/0318088 A1* | 12/2010 | Warne et al. ............... 606/87 |
| 2010/0324692 A1 | 12/2010 | Uthgenannt et al. |
| 2011/0004317 A1 | 1/2011 | Hacking et al. |
| 2011/0009869 A1* | 1/2011 | Marino et al. ............... 606/87 |
| 2011/0015636 A1 | 1/2011 | Katrana et al. |
| 2011/0015639 A1 | 1/2011 | Metzger et al. |
| 2011/0015752 A1 | 1/2011 | Meridew |
| 2011/0022049 A1* | 1/2011 | Huebner et al. ............. 606/71 |
| 2011/0029091 A1 | 2/2011 | Bojarski et al. |
| 2011/0029093 A1 | 2/2011 | Bojarski et al. |
| 2011/0029116 A1 | 2/2011 | Jordan et al. |
| 2011/0035012 A1 | 2/2011 | Linares |
| 2011/0040303 A1 | 2/2011 | Iannotti |
| 2011/0040334 A1 | 2/2011 | Kaes et al. |
| 2011/0046735 A1 | 2/2011 | Metzger et al. |
| 2011/0054478 A1 | 3/2011 | Vanasse et al. |
| 2011/0066193 A1 | 3/2011 | Lang et al. |
| 2011/0066245 A1 | 3/2011 | Lang et al. |
| 2011/0071528 A1 | 3/2011 | Carson |
| 2011/0071529 A1 | 3/2011 | Carson |
| 2011/0071530 A1 | 3/2011 | Carson |
| 2011/0071532 A1 | 3/2011 | Carson |
| 2011/0071533 A1 | 3/2011 | Metzger et al. |
| 2011/0092804 A1 | 4/2011 | Schoenefeld et al. |
| 2011/0093086 A1 | 4/2011 | Witt et al. |
| 2011/0106254 A1 | 5/2011 | Abel et al. |
| 2011/0125264 A1 | 5/2011 | Bagga et al. |
| 2011/0130795 A1* | 6/2011 | Ball ............... 606/86 R |
| 2011/0151027 A1 | 6/2011 | Clineff et al. |
| 2011/0151259 A1 | 6/2011 | Jarman-Smith et al. |
| 2011/0153025 A1 | 6/2011 | McMinn |
| 2011/0160736 A1 | 6/2011 | Meridew et al. |
| 2011/0160867 A1 | 6/2011 | Meridew et al. |
| 2011/0166578 A1 | 7/2011 | Stone et al. |
| 2011/0172672 A1 | 7/2011 | Dubeau et al. |
| 2011/0184419 A1 | 7/2011 | Meridew et al. |
| 2011/0184526 A1 | 7/2011 | White et al. |
| 2011/0190899 A1 | 8/2011 | Pierce et al. |
| 2011/0190901 A1 | 8/2011 | Weissberg et al. |
| 2011/0213376 A1 | 9/2011 | Maxson et al. |
| 2011/0214279 A1 | 9/2011 | Park et al. |
| 2011/0218545 A1 | 9/2011 | Catanzarite et al. |
| 2011/0224674 A1 | 9/2011 | White et al. |
| 2011/0238071 A1 | 9/2011 | Fernandez-Scoma |
| 2011/0251617 A1* | 10/2011 | Ammann et al. ............... 606/88 |
| 2011/0257657 A1* | 10/2011 | Turner et al. ............... 606/103 |
| 2011/0269100 A1* | 11/2011 | Furrer et al. ............... 433/72 |
| 2011/0275032 A1* | 11/2011 | Tardieu et al. ............... 433/174 |
| 2011/0295887 A1 | 12/2011 | Palmese et al. |
| 2012/0010619 A1 | 1/2012 | Barsoum |
| 2012/0010710 A1 | 1/2012 | Frigg |
| 2012/0010711 A1 | 1/2012 | Antonyshyn et al. |
| 2012/0041445 A1 | 2/2012 | Roose et al. |
| 2012/0041446 A1 | 2/2012 | Wong et al. |
| 2012/0065640 A1* | 3/2012 | Metzger et al. ............... 606/88 |
| 2012/0078254 A1 | 3/2012 | Ashby et al. |
| 2012/0078259 A1* | 3/2012 | Meridew ............... 606/87 |
| 2012/0089595 A1* | 4/2012 | Jaecksch ............... 707/714 |
| 2012/0101586 A1 | 4/2012 | Carson |
| 2012/0109137 A1 | 5/2012 | Iannotti et al. |
| 2012/0109138 A1* | 5/2012 | Meridew et al. ............... 606/91 |
| 2012/0109226 A1 | 5/2012 | Iannotti et al. |
| 2012/0123422 A1 | 5/2012 | Agnihotri et al. |
| 2012/0130382 A1 | 5/2012 | Iannotti et al. |
| 2012/0136365 A1 | 5/2012 | Iannotti et al. |
| 2012/0141034 A1 | 6/2012 | Iannotti et al. |
| 2012/0143197 A1* | 6/2012 | Lang et al. ............... 606/87 |
| 2012/0143267 A1 | 6/2012 | Iannotti et al. |
| 2012/0209276 A1 | 8/2012 | Schuster |
| 2012/0215225 A1* | 8/2012 | Philippon et al. ............... 606/87 |
| 2012/0221017 A1 | 8/2012 | Bonutti |
| 2012/0226283 A1* | 9/2012 | Meridew et al. ............... 606/81 |
| 2012/0232596 A1* | 9/2012 | Ribeiro ............... 606/289 |
| 2012/0245587 A1 | 9/2012 | Fang et al. |
| 2012/0259335 A1 | 10/2012 | Scifert et al. |
| 2012/0265208 A1* | 10/2012 | Smith ............... 606/87 |
| 2012/0271131 A1* | 10/2012 | Kling et al. ............... 600/324 |
| 2012/0271314 A1 | 10/2012 | Stemniski et al. |
| 2012/0271366 A1* | 10/2012 | Katrana et al. ............... 606/86 R |
| 2012/0276509 A1 | 11/2012 | Iannotti et al. |
| 2012/0277751 A1* | 11/2012 | Catanzarite et al. ............... 606/88 |
| 2012/0289965 A1* | 11/2012 | Gelaude et al. ............... 606/87 |
| 2012/0296339 A1* | 11/2012 | Iannotti et al. ............... 606/87 |
| 2012/0303004 A1* | 11/2012 | Uthgenannt et al. ............... 606/1 |
| 2012/0303033 A1* | 11/2012 | Weiner et al. ............... 606/87 |
| 2012/0310399 A1* | 12/2012 | Metzger ............... 700/98 |
| 2012/0316564 A1 | 12/2012 | Serbousek et al. |
| 2012/0323246 A1* | 12/2012 | Catanzarite et al. ............... 606/88 |
| 2013/0001121 A1* | 1/2013 | Metzger ............... 206/438 |
| 2013/0006250 A1* | 1/2013 | Metzger et al. ............... 606/87 |
| 2013/0035766 A1* | 2/2013 | Meridew ............... 623/22.21 |
| 2013/0085500 A1 | 4/2013 | Meridew et al. |
| 2013/0119579 A1 | 5/2013 | Iannotti et al. |
| 2013/0123850 A1 | 5/2013 | Schoenefeld et al. |
| 2013/0197528 A1 | 8/2013 | Zakaria et al. |
| 2013/0218163 A1 | 8/2013 | Frey |
| 2013/0338673 A1 | 12/2013 | Keppler |

FOREIGN PATENT DOCUMENTS

| | | | |
|---|---|---|---|
| CA | 2505371 A1 | 5/2004 | |
| CA | 2505419 A1 | 6/2004 | |
| CA | 2506849 A1 | 6/2004 | |
| CA | 2546958 A1 | 6/2005 | |
| CA | 2546965 A1 | 6/2005 | |
| CA | 2588907 A1 | 6/2006 | |
| CA | 2590534 A1 | 6/2006 | |
| CN | 1630495 A | 6/2005 | |
| CN | 1728976 A | 2/2006 | |
| CN | 1729483 A | 2/2006 | |
| CN | 1729484 A | 2/2006 | |
| CN | 1913844 A | 2/2007 | |
| CN | 101111197 A | 1/2008 | |
| DE | 3447365 A1 | 7/1986 | |
| DE | 04219939 A1 | 12/1993 | |
| DE | 4421153 A1 | 12/1995 | |
| DE | 102009028503 A1 | 2/2011 | |
| DE | 102011082902 A1 | 3/2012 | |
| DE | 102012205820 A1 | 10/2012 | |
| DE | 112010003901 T5 | 11/2012 | |
| EP | 0114505 A1 | 8/1984 | |
| EP | 0326768 A2 | 8/1989 | |
| EP | 0579868 A2 | 1/1994 | |
| EP | 0591985 A1 | 4/1994 | |
| EP | 0650706 A1 | 5/1995 | |
| EP | 0916324 A2 | 5/1999 | |
| EP | 1321107 A1 | 6/2003 | |
| EP | 1327424 A1 | 7/2003 | |
| EP | 1437102 A1 | 7/2004 | |
| EP | 01486900 A1 | 12/2004 | |
| EP | 1588669 A | 10/2005 | |
| EP | 1634551 A2 | 3/2006 | |
| EP | 1852072 A2 | 7/2007 | |
| EP | 1832239 A1 | 9/2007 | |
| EP | 1852072 A2 * | 11/2007 | ............ A61B 17/17 |
| EP | 1852072 A3 * | 11/2007 | ............ A61B 17/17 |
| EP | 2029061 A2 | 3/2009 | |
| EP | 2168507 A2 | 3/2010 | |
| EP | 2303146 A1 | 4/2011 | |
| EP | 2303192 A1 | 4/2011 | |
| EP | 2352445 A1 | 8/2011 | |
| EP | 2396741 A1 | 12/2011 | |
| EP | 2398381 A1 | 12/2011 | |
| EP | 2403437 A2 | 1/2012 | |
| EP | 2491873 A2 | 8/2012 | |
| FR | 2659226 A1 | 9/1991 | |
| FR | 2721195 A1 | 12/1995 | |
| FR | 2768916 A1 | 4/1999 | |
| GB | 2094590 A | 9/1982 | |
| GB | 2197790 A | 6/1988 | |
| GB | 2423021 | 8/2006 | |

(56) References Cited

FOREIGN PATENT DOCUMENTS

| | | |
|---|---|---|
| GB | 2442441 A | 4/2008 |
| GB | 2447702 A | 9/2008 |
| GB | 2483980 A | 3/2012 |
| GB | 2486390 A | 6/2012 |
| GB | 2490220 A | 10/2012 |
| GB | 2491526 A | 12/2012 |
| JP | 59157715 A | 9/1984 |
| JP | 60231208 A | 11/1985 |
| JP | 2011505080 A | 2/2011 |
| JP | 2011527885 A | 11/2011 |
| KR | 20050072500 A | 7/2005 |
| KR | 20050084024 A | 8/2005 |
| RU | 2083179 C1 | 7/1997 |
| RU | 2113182 C1 | 6/1998 |
| RU | 2125835 C1 | 2/1999 |
| RU | 2138223 C1 | 9/1999 |
| RU | 2175534 C2 | 11/2001 |
| RU | 2187975 C1 | 8/2002 |
| TW | 231755 | 5/2005 |
| WO | WO-8807840 A1 | 10/1988 |
| WO | WO-9107139 A1 | 5/1991 |
| WO | WO-9325157 A1 | 12/1993 |
| WO | WO-9528688 A1 | 10/1995 |
| WO | WO-9952473 A1 | 10/1999 |
| WO | WO-9959106 A1 | 11/1999 |
| WO | WO-0170142 A1 | 9/2001 |
| WO | WO-0184479 A1 | 11/2001 |
| WO | WO-0217821 A2 | 3/2002 |
| WO | WO-0226145 | 4/2002 |
| WO | WO-0236024 A1 | 5/2002 |
| WO | WO-02096268 A2 | 12/2002 |
| WO | WO-03051210 A2 | 6/2003 |
| WO | WO-03051211 A1 | 6/2003 |
| WO | WO-2004032806 A1 | 4/2004 |
| WO | WO-2004049981 A2 | 6/2004 |
| WO | WO-2004051301 A2 | 6/2004 |
| WO | WO-2004078069 A2 | 9/2004 |
| WO | WO-2005051209 A | 6/2005 |
| WO | WO-2005051239 A1 | 6/2005 |
| WO | WO-2005051240 A1 | 6/2005 |
| WO | WO-2005077039 A2 | 8/2005 |
| WO | WO-2006058057 A2 | 6/2006 |
| WO | WO-2006060795 A1 | 6/2006 |
| WO | WO-2006092600 A1 | 9/2006 |
| WO | WO-2006127486 A2 | 11/2006 |
| WO | WO-2006134345 A1 | 12/2006 |
| WO | WO-2006136955 A1 | 12/2006 |
| WO | WO-2007041375 A2 | 4/2007 |
| WO | WO-2007053572 A2 | 5/2007 |
| WO | WO-2007062079 A2 | 5/2007 |
| WO | WO-2007092841 A2 | 8/2007 |
| WO | WO-2007137327 A1 | 12/2007 |
| WO | WO-2007145937 A2 | 12/2007 |
| WO | WO-2008014618 A1 | 2/2008 |
| WO | WO-2008021494 A2 | 2/2008 |
| WO | WO-2008040961 A1 | 4/2008 |
| WO | WO-2008044055 A1 | 4/2008 |
| WO | WO-2008091358 A1 | 7/2008 |
| WO | WO-2008101090 A2 | 8/2008 |
| WO | WO-2008109751 A1 | 9/2008 |
| WO | WO-2008112996 A1 | 9/2008 |
| WO | WO-2008140748 A1 | 11/2008 |
| WO | WO-2009001083 A1 | 12/2008 |
| WO | WO-2009025783 A1 | 2/2009 |
| WO | WO-2009073781 A2 | 6/2009 |
| WO | WO-2009129063 A1 | 10/2009 |
| WO | WO-2009129067 A1 | 10/2009 |
| WO | WO-2010033431 A1 | 3/2010 |
| WO | WO-2010093902 A1 | 8/2010 |
| WO | WO-2010096553 A1 | 8/2010 |
| WO | WO-2010096557 A2 | 8/2010 |
| WO | WO-2010124164 A1 | 10/2010 |
| WO | WO-2010144705 A1 | 12/2010 |
| WO | WO-2010148103 A1 | 12/2010 |
| WO | WO-2011018458 A1 | 2/2011 |
| WO | WO-2011041398 A1 | 4/2011 |
| WO | WO-2011060536 A1 | 5/2011 |
| WO | WO-2011019797 A3 | 7/2011 |
| WO | WO-2011106711 A1 | 9/2011 |
| WO | WO-2011109260 A1 | 9/2011 |
| WO | WO-2011110374 A1 | 9/2011 |
| WO | WO-2012006444 A2 | 1/2012 |
| WO | WO-2012033821 A1 | 3/2012 |
| WO | WO-2012058344 A1 | 5/2012 |
| WO | WO-2012061042 A1 | 5/2012 |
| WO | WO-2012058353 A4 | 6/2012 |
| WO | WO-2012058355 A4 | 7/2012 |
| WO | WO-2012058349 A4 | 8/2012 |
| WO | WO-2012116206 A1 | 8/2012 |
| WO | WO-2012158917 A1 | 11/2012 |
| WO | WO-2012173929 A1 | 12/2012 |
| WO | WO-2012174008 A1 | 12/2012 |

OTHER PUBLICATIONS

International Preliminary Report on Patentability issued Apr. 7, 2009 for PCT/GB2007/003737 filed Oct. 2, 2007 of which U.S. Appl. No. 12/444,143 claims benefit.

International Search Report and Written Opinion for PCT/US2009/056670 mailed Mar. 2, 2010 claiming benefit of U.S. Appl. No. 12/211,407, filed Sep. 16, 2008 (which is a CIP of U.S. Appl. No. 12/039,849, filed Feb. 29, 2008, which is a CIP of U.S. Appl. No. 11/971,390, filed Jan. 9, 2008, which is a CIP of U.S. Appl. No. 11/756,957, filed May 31, 2007).

International Search Report and Written Opinion mailed Apr. 22, 2010 for PCT/US2010/024579 claiming benefit of U.S. Appl. No. 12/389930, filed Feb. 20, 2009.

International Search Report and Written Opinion mailed Jan. 25, 2008 for PCT/GB2007/003737 filed Oct. 2, 2007 of which U.S. Appl. No. 12/444,143 claims benefit.

Lombardi, Adolph, et al., "Patient-Specific Approach in Total Knee Arthroplasty," Knee Orthopedics, ORTHOSuperSite (Sep. 1, 2008), 5 pages, http://www.orthosupersite.com/view.aspx?rid=31419, printed May 20, 2010.

International Preliminary Report on Patentability mailed Aug. 25, 2011 for PCT/US2010/024073 filed Feb. 12, 2010, claiming benefit of U.S. Appl. No. 12/371,096, filed Feb. 13, 2009.

International Preliminary Report on Patentability mailed Sep. 1, 2011 for PCT/US2010/024579 claiming benefit of U.S. Appl. No. 12/389,930, filed Feb. 20, 2009.

International Preliminary Report on Patentability mailed Sep. 1, 2011 for PCT/US2010/024584 claiming benefit of U.S. Appl. No. 12/389,901, filed Feb. 20, 2009.

International Search Report and Written Opinion mailed Aug. 9, 2011 for PCT/US2011/026333 claiming benefit of U.S. Appl. No. 12/714,023, filed Feb. 26, 2010.

Botha, Chart P., Technical Report: DeVIDE—The Delft Visualisation and Image processing Development Environment, pp. 1-49 (May 31, 2006.)

Eckhoff, Donald G., et al., "Three-Dimensional Mechanics, Kinematics, and Morphology of the Knee Viewed in Virtual Reality," The Journal of Bone & Joint Surgery, vol. 81 (Dec. 4, 2005) pp. 71-80.

International Preliminary Report on Patentability for PCT/US2007/013223 issued Nov. 26, 2007.

International Search Report and Written Opinion for PCT/US2007/013223 mailed Nov. 26, 2007.

International Search Report and Written Opinion for PCT/US2009/039507 mailed Jul. 14, 2009.

International Search Report and Written Opinion for PCT/US2009/039578 mailed Jul. 31, 2009.

Invitation to Pay Additional Fees with Partial International Search mailed Nov. 26, 2009 for PCT/US2009/056670.

Nicholls, Paul, M.D., "Trauma Grand Rounds PMI (Patient-Matched Implants)" brochure, Biomet Orthopedics, Inc., (Feb. 29, 2000) 1 page.

Radermacher, K., et al., "Technique for Better Execution of CT Scan Planned Orthopedic Surgery on Bone Structures," Supplied by the British Library—"The world's knowledge" 2nd Congress of ISCAS Conference in Berlin Germany (Jun. 1995) pp. 933-938.

(56) References Cited

OTHER PUBLICATIONS

Sharp, S. Michael, Ph.D., Patient-Specific, Resurfacing Bi-Compartmental Arthuroplasty, Futuretech, Orthopaedic Product News (Mar./Apr. 2008) pp. 12-15.
Slammin, John et al, "Do You Have This Implant in My Size?", MDT Medical Design Technology, 3 pages, http://www.mdtmag.com/scripts/ShowPR.asp?PUBCODE=046&ACCT=0007796&IS-SUE . . . accessed Jul. 31, 2008.
"Amazing Precision. Beautiful Results. The next evolution of MAKOplasty® is here," brochure. (Feb. 2009) MAKO Surgical Corp. 6 pages.
"Knee tensor combined with laser femoral head locator," Research Disclosure. Jul. 2006. Number 507; p. 903.
"Method for constructing an allograft sleeve." Research Disclosure (Dec. 2003) No. 476, p. 1294.
International Preliminary Report on Patentability and Written Opinion for PCT/US2009/039578 mailed Oct. 28, 2010 claiming benefit of U.S. Appl. No. 12/103,834, filed Apr. 16, 2008.
International Preliminary Report on Patentability and Written Opinion mailed Oct. 28, 2010 for PCT/US2009/039507 claiming benefit of U.S. Appl. No. 12/103,824, filed Apr. 16, 2008.
International Preliminary Report on Patentability for PCT/US2007/013223 mailed Dec. 24, 2008 claiming benefit of U.S. Appl. No. 11/756,057, filed May 31, 2007.
International Preliminary Report on Patentability mailed Mar. 31, 2011 for PCT/US2009/056670 claiming benefit of U.S. Appl. No. 12/211,407, filed Sep. 16, 2008.
International Search Report and Written Opinion mailed Aug. 19, 2010 for PCT/US2010/024584 claiming benefit of U.S. Appl. No. 12/389,901, filed Feb. 20, 2009.
International Search Report and Written Opinion mailed Dec. 7, 2010 for PCT/US2010/050701 claiming benefit of U.S. Appl. No. 12/571,969, filed Oct. 1, 2009.
International Search Report and Written Opinion mailed Jun. 10, 2010 for PCT/US2010/038177 claiming benefit of U.S. Appl. No. 12/483,807, filed Jun. 12, 2009.
International Search Report and Written Opinion mailed Jun. 4, 2010 for PCT/US2010/024073 filed Feb. 12, 2010, claiming benefit of U.S. Appl. No. 12/371,096, filed Feb. 13, 2009.
International Search Report and Written Opinion mailed May 9, 2011 for PCT/US2011/026412 claiming benefit of U.S. Appl. No. 12/872,663, filed Aug. 31, 2010.
International Search Report and Written Opinion mailed Oct. 5, 2010 for PCT/US2010/038845 claiming benefit of U.S. Appl. No. 12/486,992, filed Jun. 18, 2009.
Invitation to Pay Additional Fees mailed May 3, 2011 for PCT/US2011/026333 claiming benefit of U.S. Appl. No. 12/714,023, filed Feb. 26, 2010.
Radermacher, Klaus, et al. "Computer Assisted Orthopaedic Individual Templates." Clinical Orthopaedics and Related Research. (Sep. 1998) No. 354; pp. 28-38.
"Ascent Total Knee System," brochure. Biomet, Inc. (Oct. 31, 1999) 16 sheets.
"Customized Patient Instruments, Patient specific instruments for patient specific needs," brochure. (2008) DePuy Orthopaedics, Inc. 14 sheets.
"Customized Patient Instruments, Primary Cruciate Retaining Surgical Technique for use with the Sigma® Knee System Utilizing Specialist® 2 Instrumentation," brochure. (2008) DePuy Orthopaedics, Inc. pp. 1-23.
"Discovery® Elbow System Surgical Technique," brochure. Biomet Orthopedics, Inc. (Dec. 31, 2008) pp. 1-25.
"Discovery® Elbow System," brochure. Biomet Orthopedics, Inc. (Nov. 30, 2007) 3 sheets.
"OSS™ Orthopaedic Salvage System, Femoral/Tibial Augmentation," brochure. Biomet Orthopedics, Inc., (Mar. 31, 2004) pp. 1-8 (12 sheets).
"Patient Matched PMI Implants, C.A.M.R.A. 3-D Imaging," brochure, Biomet, Inc. (Jan. 31, 1991) 6 pages.

"Regenerex® Tibial Cone Augment, Surgical Technique Addendum to the Vanguard® SSK Revision System," brochure. Biomet® Orthopedics. (revised Mar. 31, 2010) pp. 1-8 (12 sheets).
"Signature™ Personalized Patient Care, Surgical Technique Addendum to the Vanguard Knee System" brochure. Biomet® Orthopedics, Inc. (May 15, 2009) pp. 1-8.
"TruMatch™ Personalized knee replacement solutions," tri-fold brochure. (2009) SIGMA® DePuy Orthopaedics, Inc. 2 pages.
"Vanguard® PFR Partial Knee Patellofemoral Replacement System," Surgical Technique brochure. Biomet Orthopaedics, (revised Aug. 31, 2010) pp. 1-25.
"Zimmer® UniSpacer® Knee System," brochure. (2005) Zimmer, Inc. 4 sheets.
Birnbaum, Klaus, M.D., "Computer-Assisted Orthopedic Surgery With Individual Templates and Comparison to Conventional Method," SPINE vol. 26, No. 4, pp. 365-370 (2001) Lippincott Williams & Wilkins, Inc.
Cohen, Zohara A., et al. "Knee cartilage topography, thickness, and contact areas from MRI: in-vitro calibration and in-vivo measurements." Journal of the OsteoArthritis Research Society International. Osteoarthritis and Cartilage, (1999) vol. 7; No. 1 pp. 95-109.
Fortin, Thomas, D.D.S., Ph.D., et al., "Precise Dental Implant Placement in Bone Using Surgical Guides in Conjunction with Medical Imaging Techniques," Journal of Oral Implantology, Clinical, vol. 26, No. 4 (2000) pp. 300-303.
Haaker, R.G., et al., "Minimal-invasive navigiert implantierte unikondyläre Knieendoprothese," Orthopäde 2006 35:1073-1079 (Sep. 13, 2006) Spinger Medizin Verlag.
Hafez, M.A., et al., "Computer-assisted Total Knee Arthroplasty Using Patient-specific Templating," Clinical Orthopaedics and Related Research, No. 444 (pp. 184-192) 2006 Lippincott Williams & Wilkins.
Hazen, Eric J., M.D., "Computer-Assisted Orthopaedic Sugery, A New Paradigm," Techniques in Orthopaedics® vol. 18, No. 2, (2003) pp. 221-229.
Hutmacher, Dietmar, W., "Scaffolds in tissue engineering bone and cartilage," Biomaterials, 2000 Elsevier Science Ltd. (pp. 2529-2543).
Kaus, Michael R., Ph.D., "Automated Segmentation of MR Images of Brain Tumors," Radiology, vol. 218, No. 2, (2001) pp. 586-591.
Klein, M., "Robot assisted insertion of craniofacial implants—clinical experience," CARS 2001, pp. 133-138 (2001) Elsevier Science B.V.
Lynch, John A., et al., "Cartilage segmentation of 3D MRI scans of the osteoarthritic knee combining user knowledge and active contours," Medical Imaging 2000: Image Processing SPIE vol. 3979 (2000) pp. 925-935.
Overhoff, H.M., et al., "Total Knee Arthroplasty: Coordinate System Definition and Planning based on 3-D Ultrasound Image Volumes," CARS 2001, pp. 283-288, (2001) Elsevier Science B.V.
Portheine, F., "CT-basierte Planung und DISOS-Schablonennavigation in der Kniegelenkendoprothetik," in Navigation und Robotic in der Gelenk—und Wirbelsäulenchirugie, Kapitel 32, Springer Verlag (2003) pp. 262-269.
Portheine, F., et al., Entwicklung eines klinischen Demonstrators für die computerunterstützte Orthopädische Chirurgie mit CT-Bildbasierten Individualschablonen, Bildverarbeitung fur die Medizin (1998) 5 pages.
Portheine, K., "Development of a clinical demonstrator for computer assisted orthopedic surgery with CT-image based individual templates," Computer Assisted Radiology and Surgery, pp. 944-949, (1997) Elsevier Science B.V.
Radermacher, "Computer Assisted Orthopaedic Surgery with Image Based Individual Templates," Clinical Orthopaedics and Related Research No. 354, pp. 28-38 (Sep. 1998) Lippincott Williams & Wilkins.
Radermacher, K., et al., "Computer Integrated Orthopaedic Surgery: Connection of Planning and Execution in Surgical Intervention," Computer-integrated surgery: technology and clinical applications, (1996) pp. 451-463.
Radermacher, K., et al., "CT Image-Based Planning and Execution of Interventions in Orthopedic Surgery Using Individual Templates,

(56) References Cited

OTHER PUBLICATIONS

Experimental Results and Aspects of Clinical Applications," Computer Assisted Orthopedic Surgery (CAOS), pp. 42-52, (1995) Hogrefe & Huber Publishers.

Radermacher, K., et al., "Image Guided Orthopedic Surgery Using Individual Templates," Springer Berlin/Heidelberg, CVRMed-MRCAS'97, vol. 1205/1997 pp. 606-615), (1997).

Schuller-Götzburg, P., et al., 3D-Implantatplanung und Stereolithographie-Implantatbohrschablonen, Stomatologie 101.3, pp. 55-59 (May 2004).

Sisto, Domenick, J., et al., "Custom Patellofemoral Arthroplasty of the Knee Surgical Technique," Journal of Bone and Joint Surgery, vol. 89-A, pp. 214-225 (Jul. 2006).

Steinwachs, Matthias Reinhard, "Cartilage Repair—Autologous Chondrocyte Transplantation and Autologous Matrix-induced Chondrogenesis," European Musculoskeletal Review (2006) pp. 65-68.

Great Britain Search Report mailed Dec. 21, 2011 for GB1116054.6, claiming benefit of U.S. Appl. No. 12/888,005, filed Sep. 22, 2010.

International Preliminary Report and Written Opinion mailed Jan. 5, 2012 for PCT/US2010/038845 claiming benefit of U.S. Appl. No. 12/486,992, filed Jun. 18, 2009.

International Preliminary Report on Patentability and Written Opinion mailed Dec. 22, 2011 for PCT/US2010/038177 claiming benefit of U.S. Appl. No. 12/483,807, filed Jun. 12, 2009.

International Search Report mailed Nov. 30, 2010 for PCT/EP2010/061630 filed Aug. 10, 2010 claiming benefit of DE102009028503.2 filed Aug. 13, 2009.

Supplementary European Search Report mailed Nov. 15, 2011 for EP07809326, which claims benefit of PCT/US2007/013223, filed Jun. 5, 2007; which claims priority to U.S. Appl. No. 11/756,057, filed May 31, 2007.

Friedman, R.J. et al., "The Use of Computerized Tomography In The Measurement of Glenoid Version", Journal of Bone & Joint Surgery Am. (JBJS) 1992;74:1032-1037 (Aug. 1992).

International Search Report and Written Opinion mailed Dec. 18, 2012 for PCT/US2012/059189, which claims benefit of U.S. Appl. No. 13/597,478 filed Aug. 29, 2011.

International Search Report and Written Opinion mailed Feb. 6, 2013 for PCT/US2012/060842, which claims benefit of U.S. Appl. No. 13/653,868 filed Oct. 17, 2012.

International Search Report and Written Opinion mailed Feb. 6, 2013 for PCT/US2012/060854, which claims benefit of U.S. Appl. No. 13/653,893 filed Oct. 17, 2012.

International Search Report and Written Opinion mailed Nov. 15, 2012, for PCT/US2012/052853, which claims benefit of U.S. Appl. No. 13/221,968 filed Aug. 31, 2011.

International Search Report mailed Oct. 23, 2012, for PCT/US2012/041893, which claims benefit of U.S. Appl. No. 61/496,177 filed Jun. 13, 2011.

Invitation to Pay Additional Fees mailed Feb. 6, 2013 for PCT/US2012/060848, which claims benefit of U.S. Appl. No. 13/653,878 filed Oct. 17, 2012.

Invitation to Pay Additional Fees mailed Feb. 7, 2013 for PCT/US2012/060853, which claims benefit of U.S. Appl. No. 13/653,893 filed Oct. 17, 2012.

International Search Report and Written Opinion for PCT/US2013/026875 mailed Jun. 7, 2013, claiming benefit of U.S. Appl. No. 13/400,652, filed Feb. 21, 2012.

International Preliminary Report on Patentability mailed Sep. 6, 2013 for PCT/US2012/026356 claiming benefit of U.S. Appl. No. 13/041,883 filed Mar. 7, 2011.

International Search Report and Written Opinion mailed Oct. 14, 2013 for PCT/US2013/057097 claiming benefit of U.S. Appl. No. 13/597,478 filed Aug. 29, 2012.

International Preliminary Report on Patentability for PCT/US2010/050701 mailed Apr. 12, 2012 claiming benefit of U.S. Appl. No. 12/571,969, filed Oct. 1, 2009.

International Search Report and Written Opinion mailed Mar. 5, 2012 for PCT/US2011/057300 claiming benefit of U.S. Appl. No. 12/938,905, filed Nov. 3, 2010.

International Search Report and Written Opinion mailed May 8, 2012 for PCT/US2012/026356 claiming benefit of U.S. Appl. No. 13/041,883, filed Mar. 7, 2011.

Thoma, W., et al., "Endoprothetischen Versorgung des Kniegelenks auf der Basis eines 3D-computertomographischen Subtraktionsverfahrens," Zuma Thema: Computergestutzte orthopädische Chirugie, Der Orthopäde 29:641-644 Springer-Verlag (Jul. 2000) Translation provided: Thoma, W., "Endoprosthetic care of the knee joint based on a 3D computer chromatography subtraction process," Topic: Computer-aided orthopedic surgery. Orthopedist 2000 29:641-644 Springer Verlag (Jul. 2000).

Biomet "Oxford® Partial Knee" brochure, 8 pages (Feb. 2011).

Biomet "The Oxford® Partial Knee Surgical Technique," brochure, pp. 1-38, (Feb. 2010).

Biomet, "Oxford® Partial Knee Microplasty® Instrumentation Surgical Technique", brochure, pp. 1-54 (May 2011).

International Preliminary Report on Patentability and Written Opinion mailed Sep. 7, 2012 for PCT/US2011/026333 claiming benefit of U.S. Appl. No. 12/714,023, filed Feb. 26, 2010.

International Preliminary Report on Patentability and Written Opinion mailed Jan. 3, 2014 for PCT/US2012/042081 claiming benefit of U.S. Appl. No. 13/493,509, filed Jun. 11, 2012.

International Preliminary Report on Patentability and Written Opinion mailed Nov. 28, 2013 for PCT/US2012/038351 claiming benefit of U.S. Appl. No. 13/111,007, filed May 19, 2011.

\* cited by examiner

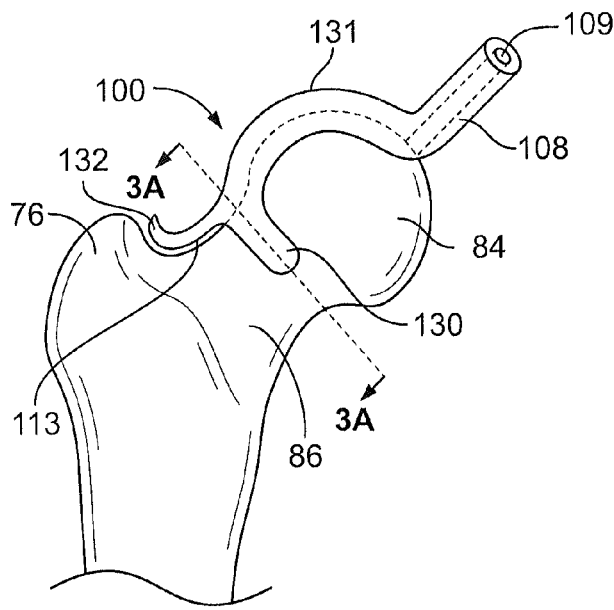 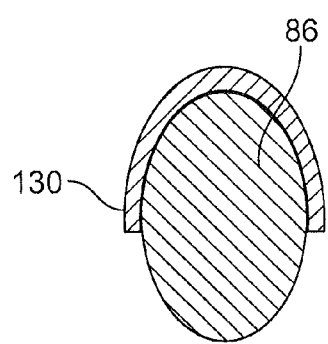
FIG. 3    FIG. 3A
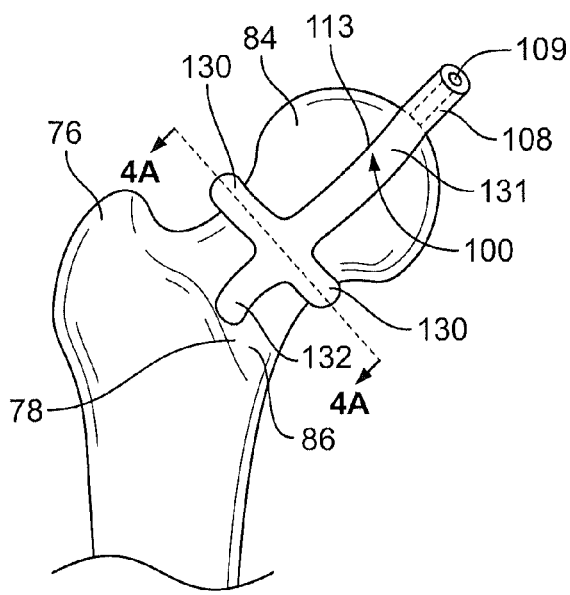 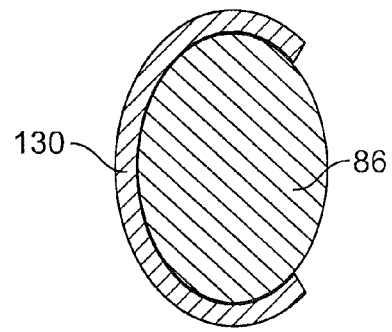
FIG. 4    FIG. 4A

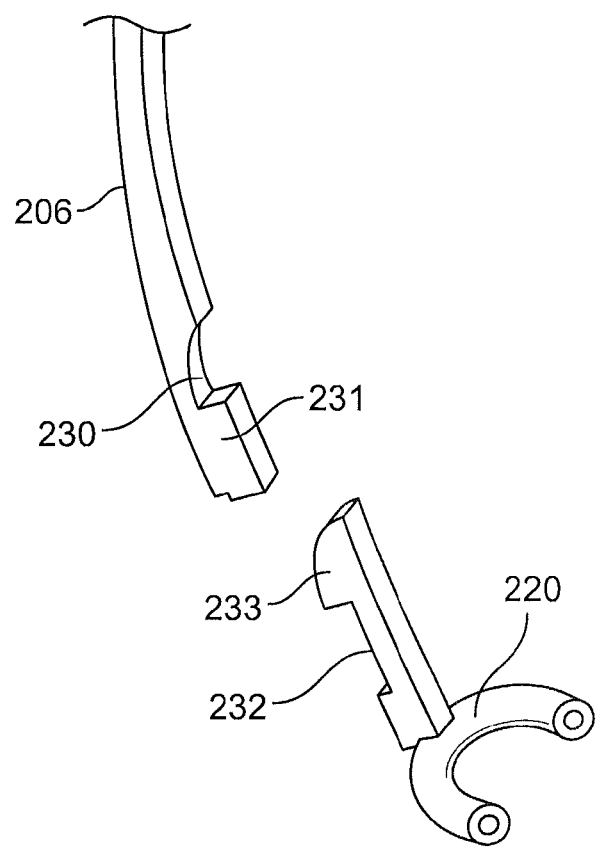
FIG. 7B
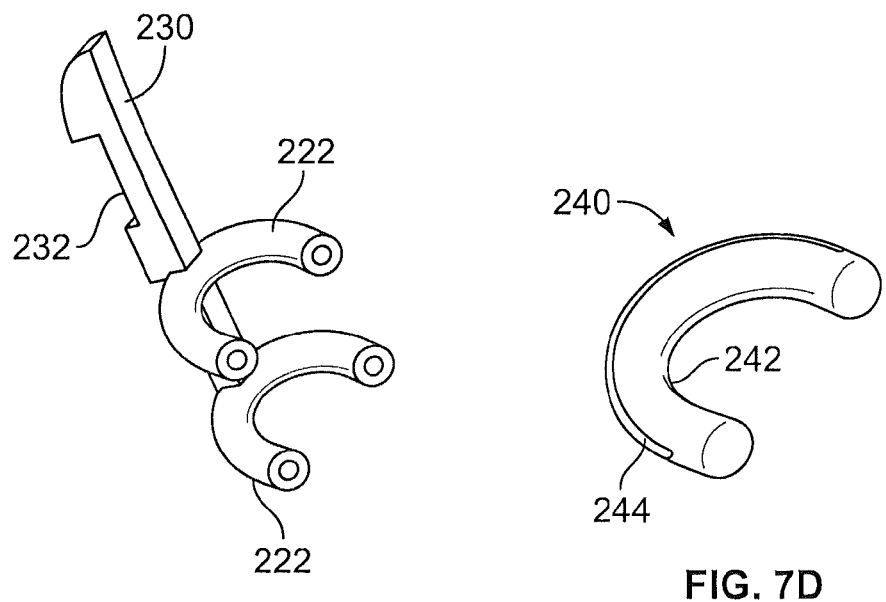
FIG. 7C
FIG. 7D

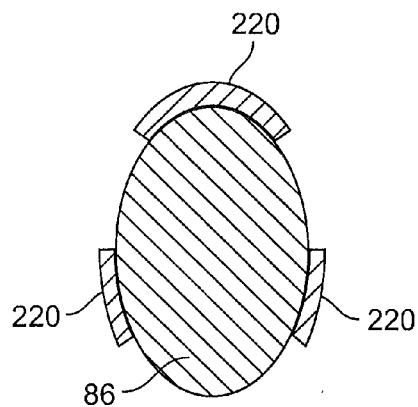
FIG. 8B
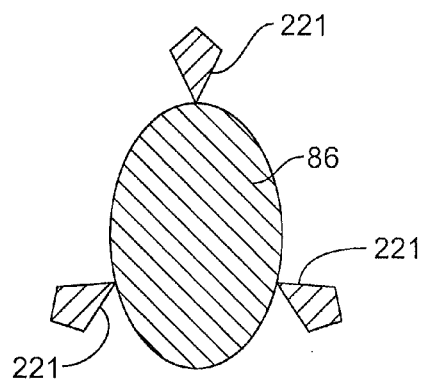
FIG. 8C
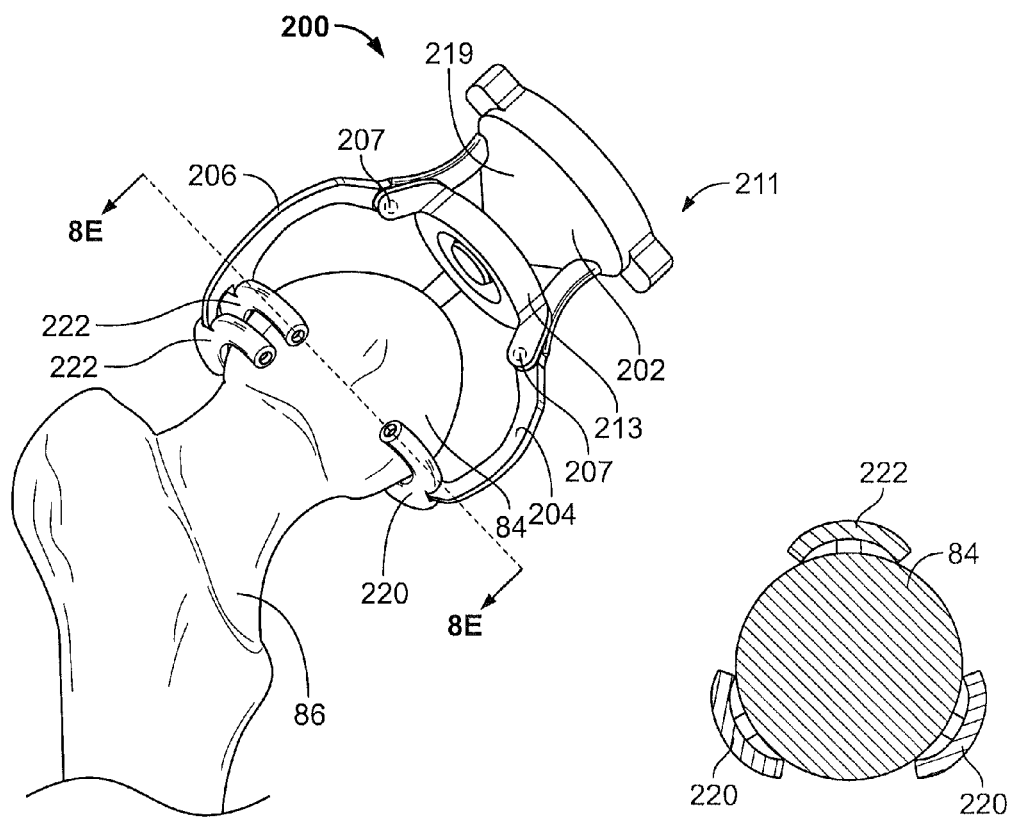
FIG. 8D
FIG. 8E

PATIENT-SPECIFIC ALIGNMENT GUIDE

CROSS-REFERENCE TO RELATED APPLICATIONS

This application is a continuation-in-part of U.S. application Ser. No. 12/039849, filed on Feb. 29, 2008, now U.S. Pat. No. 8,282,646, which claims the benefit of provisional application 60/892349, filed Mar. 1, 2007, and which is a continuation-in-part of U.S. application Ser. No. 11/756057, filed on May 31, 2007, now U.S. Pat. No. 8,092,465, which claims the benefit of U.S. Provisional Application No. 60/812694, filed on Jun. 9, 2006.

This application is also a continuation-in-part of U.S. application Ser. No. 12/025414, filed on Feb. 4, 2008, now U.S. Pat. No. 8,298,237, which claims the benefit of U.S. Provisional Application No. 60/953637, filed on Aug. 2, 2007.

The disclosures of the above applications are incorporated herein by reference.

INTRODUCTION

Various custom made, patient-specific orthopedic implants and associated templates and alignment guides are known in the art. Such implants and guides can be developed using commercially available software. Custom implant guides are used to accurately place pins, guide bone cuts, and insert implants during orthopedic procedures. The guides can be made from a pre-operative plan formed from MRI or CT scans of the patient and rely on matching a subcutaneous anatomic feature for correct positioning.

The present teachings provide a patient-specific alignment guide for a femoral resurfacing or replacement procedure.

SUMMARY

The present teachings provide an orthopedic apparatus including an alignment guide attachable to a femoral joint surface of a femur of a patient. The alignment guide has a patient-specific three-dimensional engagement surface, and at least one guiding portion defining a guiding passage. The engagement surface anatomically matches a corresponding portion of the femoral joint surface.

The present teachings provide an orthopedic apparatus including a frame including a body and a longitudinal post extending from the body, a securing member threadably couplable to the post; and a plurality of arms coupled to the body and movable between an open configuration and a closed configuration. The plurality of arms can be engaged to a femoral joint surface of a patient in the closed configuration. Each arm has a clamping portion with a patient-specific three-dimensional engagement surface. The engagement surface anatomically matches a corresponding portion of the femoral joint surface.

In various embodiments, the present teachings provide an orthopedic apparatus including a reusable frame having a body and a plurality of arms coupled the body. The plurality of arms can be engaged to a femoral joint surface of a patient. The apparatus also includes a plurality of disposable clamping portions. Each clamping portion can be removably coupled to a corresponding arm, and each clamping portion can include a patient-specific three-dimensional engagement surface. The engagement surface anatomically matches a corresponding portion of the femoral joint surface of the patient.

Further areas of applicability of the present invention will become apparent from the description provided hereinafter. It should be understood that the description and specific examples are intended for purposes of illustration only and are not intended to limit the scope of the invention.

BRIEF DESCRIPTION OF THE DRAWINGS

The present invention will become more fully understood from the detailed description and the accompanying drawings, wherein:

FIG. 3 is an environmental view of a patient-specific guide according to the present teachings;

FIG. 3A is a sectional view of FIG. 3 taken along axis 3A;

FIG. 4 is an environmental view of a patient-specific guide according to the present teachings;

FIG. 4A is a sectional view of FIG. 4 taken along axis 4A;

FIG. 7B is an exploded view of an exemplary modular component of the patient-specific guide of FIG. 7;

FIG. 7C is an exploded view of an exemplary modular component of the patient-specific guide of FIG. 7;

FIG. 7D is an exploded view of an exemplary component of the patient-specific guide of FIG. 7;

FIG. 8B is an environmental sectional view of a patient-specific component of a guide according to the present teachings;

FIG. 8C is an environmental sectional view of a patient-specific component of a guide according to the present teachings, the sectional view taken along a plane perpendicular to the axis of a femoral neck of a patient;

FIG. 8D is an environmental perspective view of a patient-specific guide according to the present teachings;

FIG. 8E is a sectional view of FIG. 8D taken along axis 8E; and

DESCRIPTION OF VARIOUS EMBODIMENTS

The following description is merely exemplary in nature and is in no way intended to limit the scope of the present teachings, applications, or uses. For example, although the present teachings are illustrated for alignment guides in knee surgery, the present teachings can be used for other guides, templates, jigs, drills, rasps or other instruments used in various orthopedic procedures.

The present teachings provide a method for preparing patient-specific alignment guides for use in orthopedic surgery for a joint, such as, for example, the knee joint. Conventional, not patient-specific, prosthesis components available in different sizes can be used with the alignment guides, although patient-specific femoral and tibial prosthesis components prepared with computer-assisted image methods can also be used. Computer modeling for obtaining three dimensional images of the relevant patient's anatomy, patient-specific prosthesis components, and the alignment guides and templates can be provided by various CAD programs and/or software available from various vendors or developers, such as, for example, from Materialise USA, Ann Arbor, Mich.

Figure 1:
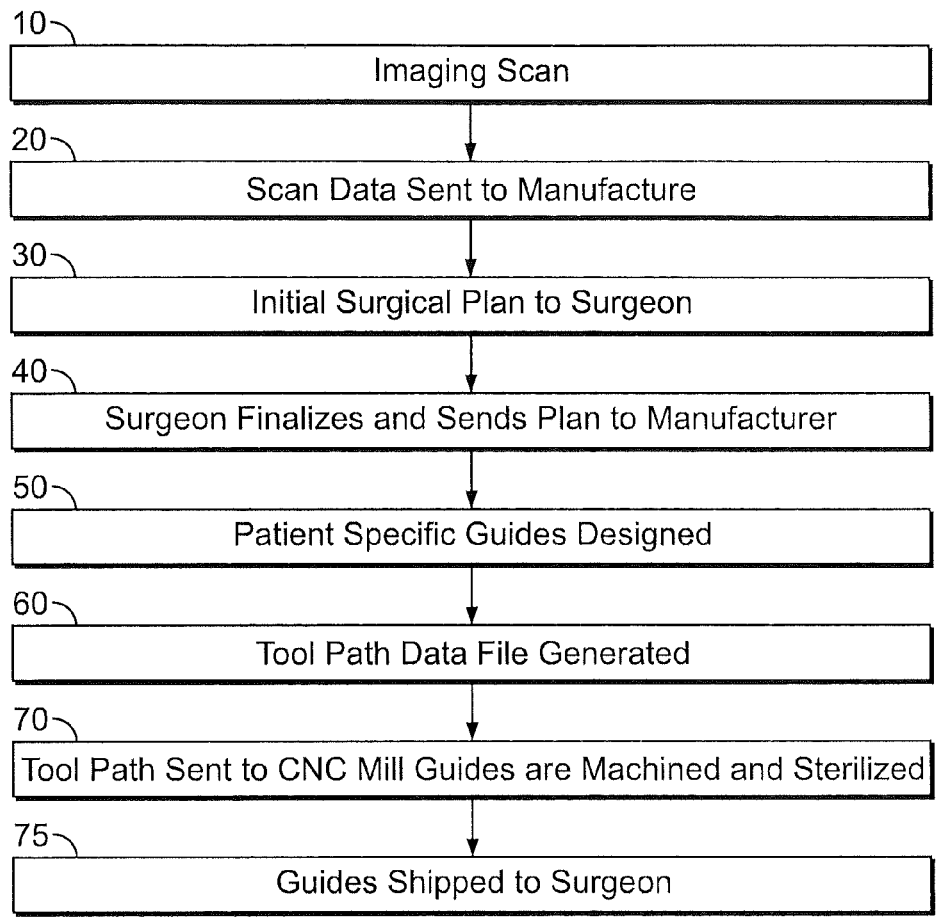
FIG. 1 is a flowchart of an exemplary method of preparing patient specific alignment guides according to the present teachings.

Referring to FIG. 1, in preoperative planning, imaging data can be obtained of an entire leg including a joint to be reconstructed at a medical facility or doctor's office, at aspect 10. The imaging data can include a detailed scan of a hip, knee and ankle. The imaging data can be obtained using MRI, CT, X-Ray, ultrasound or any other imaging system. In some cases, the scan may be performed with the patient wearing an unloader brace to stress the ligaments. The scan data obtained can be sent to a manufacturer, at aspect 20. The scan data can be used by the manufacturer to construct a three-dimensional image of the joint and prepare an initial implant fitting and alignment protocol detailing the fit of the implant. The fitting and alignment protocol can be stored in any computer storage medium, in a computer file form or any other computer or digital representation. The initial implant fitting and alignment protocol can be obtained using standard alignment methods or using alignment methods provided by or based on the preferences of individual surgeons.

As discussed above, in the preoperative planning stage of a surgical procedure, multiple image scans of portions of the patient's anatomy related to the procedure are obtained. Image markers visible in the scan can be placed on the patient's anatomy to allow image scaling and orientation. The obtained scans of the desired anatomy can be correlated to one another to reconstruct an image of the patient's specific anatomy in three-dimensions.

The outcome of the initial fitting is an initial surgical plan that can be printed or represented in electronic form with corresponding viewing software. The initial surgical plan can be surgeon-specific, when using surgeon-specific alignment protocols. The initial surgical plan, in a computer file form associated with interactive software, can be sent to the surgeon, or other medical practitioner, for review, at 30. Using the interactive software, the surgeon can manipulate the position of images of various implant components relative to an image of the joint. The surgeon can modify the plan and send it to the manufacturer with recommendations or changes. The interactive review process can be repeated until a final, approved plan is sent to the manufacturer, at 40.

Various methods of sending the initial and final surgeon-approved surgical plans can be used. The surgical plans can be, for example, transferred to an electronic storage medium, such as CD, DVD, flash memory, which can then be mailed using regular posting methods. In various embodiments, the surgical plan can be e-mailed in electronic form or transmitted through the internet or other web-based service.

After the surgical plan is approved by the surgeon, patient-specific alignment guides for the femur and tibia can be developed using a CAD program or other three-dimensional modeling software, such as the software provided by Materialise, for example, according to the surgical plan, at 50. Computer instructions of tool paths for machining the patient-specific alignment guides can be generated and stored in a tool path data file, at 60. The tool path can be provided as input to a CNC mill or other automated machining system, and the alignment guides can be machined from polymer, ceramic, metal or other suitable material, and sterilized, at 70.

The sterilized alignment guides can be shipped to the surgeon or medical facility, at 75 for use during the surgical procedure. Patient-specific components or portions are defined as those constructed by a surgical plan approved by the doctor using three-dimensional images of the specific patient's anatomy and made to closely conform and mate substantially as a negative mold of corresponding portions of the patient's anatomy, including bone surfaces with or without associated soft tissue, such as articular cartilage, for example.

Images of the knee joint anatomy can include images of the joint surfaces of the distal femur and proximal tibial with or without the associated soft tissues, such as articular cartilage, on the respective bone surfaces. The alignment procedure can make use of the mechanical, anatomic, transepicondylar and cylindrical axes in various degrees. Multiple alignment procedures can be provided to accommodate the experience and preference of individual surgeons. For example, the alignment procedure can be based on the anatomic and mechanical axes, or can be substantially based on the cylindrical axis. Further, the alignment procedure can be deformity-specific, such that the procedure is adapted, for example, to a valgus or varus deformity.

Similarly, images of the hip joint anatomy of the joint surface of the proximal femur with or without the associated soft tissues, such as articular cartilage, on the respective bone surfaces can be used in the alignment procedure. The alignment procedure can include, for example, the selection of an anteversion angle, a femoral neck angle and other orientations for positioning a femoral implant, such as a resurfacing component, without notching or impinging on the femoral neck.

Figure 2:
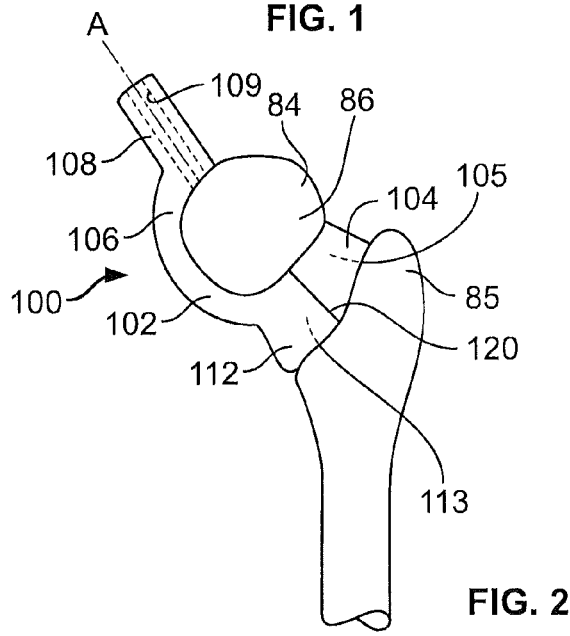
FIG. 2 is an environmental view of a patient-specific guide according to the present teachings.

Referring to FIG. 2, an exemplary multiple-component femoral alignment guide 100 that can be manufactured using the method of FIG. 1 is illustrated. In this exemplary embodiment, the alignment guide 100 is shown with first and second adjacent components 102 and 104, although more than two components can be similarly included in the alignment guide 100. The first and second components 102, 104 can be movably and/or removably connected to one another with a coupling mechanism referenced at 120. The coupling mechanism 120 can be selected from a variety of mechanisms that provide easy intra-operative assembly. In various embodiments, for example, the coupling mechanism 120 can be a snap-on connection between the two components. In various embodiments, the coupling mechanism 120 can be an interlocking mechanism, such as a keyway-and-key mechanism, a dovetail mechanism, a puzzle-like interlocking mechanism, or any other interlocking mechanism. In various embodiments, the coupling mechanism 120 can include a permanent or temporary hinge or other pivotable structure that allows relative motion between the adjacent components, such that one component can be rotated relative to the other component for ease of positioning on the patient. The components can be permanently pivotably coupled with the hinge or can be detachable.

The exemplary alignment guide 100 can be configured as patient-specific for the femoral neck 86 of a proximal femur, as illustrated in FIG. 2. The alignment guide 100, when assembled, can wrap around and mate in three dimensions with the femoral neck 86 for assisting in the placement of an alignment pin for femoral head resurfacing. The first component 102 can include a guiding portion or formation 108 and a portion 112 having a first three-dimensional inner bone engagement surface 113 that can anatomically match or mate with a portion of the femoral neck 86 in three dimensions. The guiding formation 108 can be in the form of a sleeve including a guiding passage 109, a bore, a hole, or other opening through which an alignment pin or drill bit or other tool or fastener can be inserted. The second component 104 can be coupled to the first component 102 by the coupling mechanism 120. The second component 104 can include a second three-dimensional inner bone engagement surface 105 that can anatomically match and mate with substantially the remaining portion of the femoral neck 86 in three dimensions, without requiring other supports to retain the guide 100 on the proximal femur.

Figures 5, 5A:
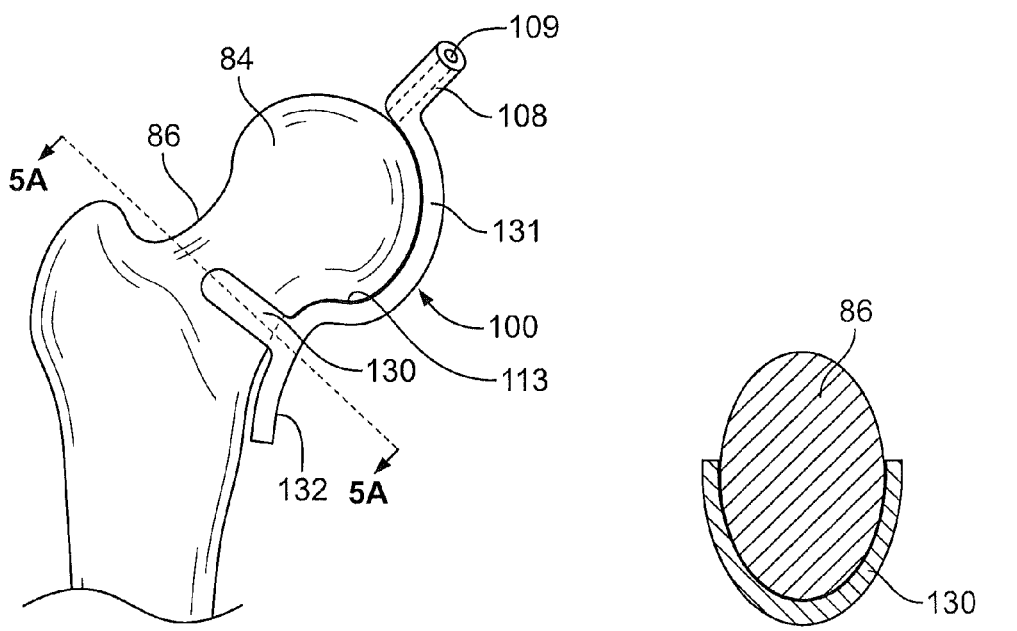
FIG. 5 is an environmental view of a patient-specific guide according to the present teachings.
FIG. 5A is a sectional view of FIG. 5 taken along axis 5A.

FIGS. 3-5 illustrate various exemplary patient-specific, unitary or single-component alignment guides 100 for the patient's proximal femur. Same reference numbers are used to refer to similar parts or features throughout various embodiments. New or additional elements are identified with new reference numbers.

Referring to FIGS. 3 and 3A, a patient-specific alignment guide 100 according to the various embodiments can be constructed as a one-piece integral or monolithic component that has a three-dimensional inner patient-specific engagement surface 113 conforming to the corresponding anatomy of a specific patient, including subchondral bone with or without soft tissue. The alignment guide 100 can include first and second arms 130 that are patient-specific, curved and substantially concave toward the femoral neck 86 and extend anteriorly and posteriorly around the femoral neck 86 without, however, fully encircling the femoral neck 86. The alignment guide 100 can be generally saddle-shaped and can include a first portion 131 conforming to a portion of the femoral head 84. The first portion 131 can be patient-specific, curved and substantially concave toward the femoral head 84. A guiding portion 108 with an internal passage 109 can extend from the first portion 131 for guiding a pin, a drill bit or other tool. The alignment guide 100 can also include a second portion 132 extending from the first portion 131 along the femoral neck 86 and abutting the greater trochanter 76. The second portion 132 can be patient-specific, conforming to the anatomy of the femoral neck 86, such that the second portion 132 can be, for example, convex where the anatomy of the femoral neck. 86 is concave. The first portion 131, the second portion 132 and the first and second arms 130 form the saddle shape of the alignment guide 100, as shown in FIG. 3. The engagement surface 113 includes the inner surfaces of the first portion 131, the second portion 132 and the first and second arms 130. The first and second arms 130 can be oriented substantially perpendicularly to the first and second portions 131, 132. The alignment guide 100 can be positioned superiorly relative to the femur, as shown in FIG. 3.

Referring to FIGS. 4 and 4A, an alignment guide 100 according to the various embodiments can include a second portion 132 that can abut the lesser trochanter 78 of the patient's femur. In the embodiment illustrated in FIG. 4, the alignment guide 100 can be positioned anteriorly or posteriorly relative to the femur and the first and second arms 130 can extend superiorly and inferiorly relative to the femur. The alignment guide 100 shown in FIG. 4 can be substantially saddle-shaped and patient-specific in three dimensions. The first portion 131 is patient-specific, curved and substantially concave inward and toward the femoral head 84. The second portion 132 is patient-specific, curved and substantially convex inward and toward the neck, and the first and second arms 130 are patient-specific, curved and substantially concave inward and toward the femoral neck 86. The engagement surface 113 includes the inner surfaces of the first portion 131, the second portion 132 and the first and second arms 130. The first and second arms 130 can be oriented substantially perpendicularly to the first and second portions 131, 132.

Referring to FIGS. 5 and 5A, an alignment guide 100 according to various embodiments can be positioned inferiorly relative to the femur and the first and second arms 130 can extend around the femoral neck 86 posteriorly and anteriorly relative to the femur. The alignment guide 100 shown in FIG. 5 is also saddle-shaped and patient-specific in three dimensions, with the first portion 131 being patient-specific, curved and substantially concave inward and toward the femoral head 84, the second portion 132 being patient-specific, curved and substantially convex inward and toward the neck, and the first and second arms 130 being curved and concave inward and toward the femoral neck 86. The engagement surface 113 includes the inner surfaces of the first portion 131, the second portion 132 and the first and second arms 130. The first and second arms 130 can be oriented substantially perpendicularly to the first and second portions 131, 132.

The alignment guides 100 shown in FIGS. 3A-5A can be made of biocompatible polymer or other material such that the first and second arms 130 that can flex to allow the alignment guide 100 to be snap on and held around the femoral neck 86 without any other temporary fixation. The alignment guide 100 can be also supported on the femur with removable fixators, such as pins.

Figures 6, 6A, 6B:
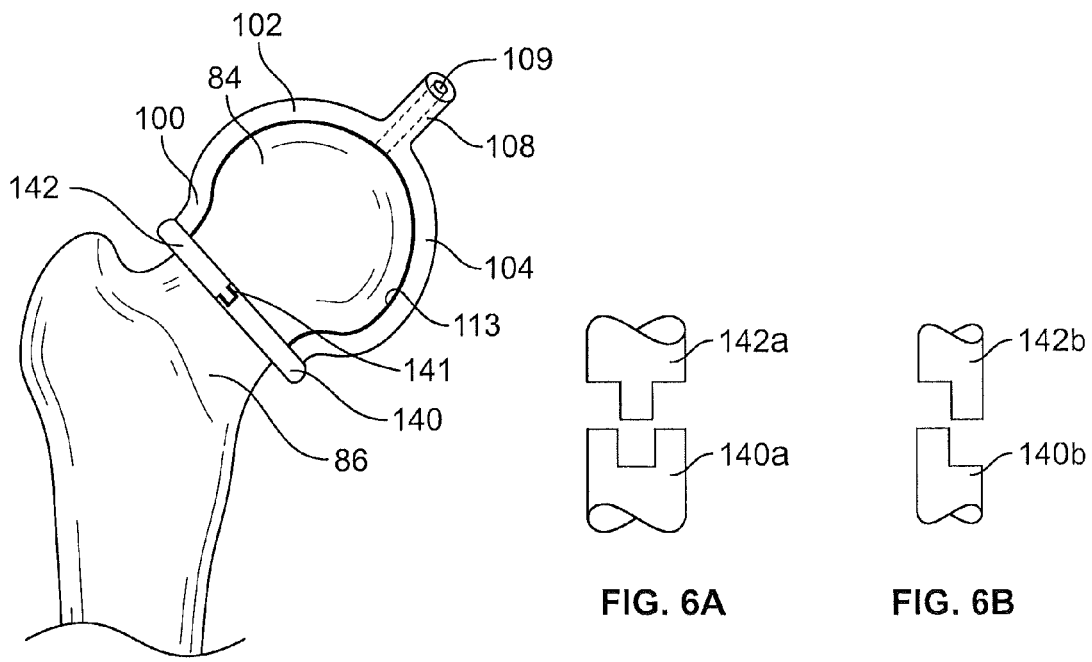
FIG. 6 is an environmental view of a patient-specific guide according to the present teachings.
FIG. 6A is an exploded view of an exemplary connection for patient-specific guide of FIG. 6.
FIG. 6B is an exploded view of an exemplary connection for patient-specific guide of FIG. 6.

In various embodiments, and referring to FIGS. 6, 6A and 6B, the alignment guide 100 can be in the form of a complete or partial shell encompassing the femoral head 84 and having a patient-specific three-dimensional inner engagement surface 113. The alignment guide 100 can include first and second members 102, 104 coupled with first and second connecting portions 140, 142 at a connection 141. In various embodiments, the first and second members 102, 104 can be flexible such that the alignment guide 100 can be mounted by opening up the connecting portions 140, 142 at one or more connections 141. In various embodiments, the first and second members 102, 104 can also include a hinge or a split connection (not shown) opposite to the connection 141. The first and second members 102, 104 can be patient-specific and curved, as shown in FIG. 6, with the inner surface 113 closely conforming to the substantially convex surface of the head 84 and to the substantially concave surface of the neck 86. The first and second connecting portions 140, 142 can form a tongue and groove connection (142a, 140a) or a other clasp or snap-on connection (142b, 140b), as shown in the exemplary illustrations of FIGS. 6A and 6B.

It will be appreciated that other single or multiple-component guides can be similarly constructed for guiding and preparing other bone joints for receiving prosthetic components. Patient-specific guides can be, for example, constructed for the knee, the hip, the shoulder, etc, and can include two or more relatively movable and interconnected components. When more than two components are used, the same or different coupling mechanisms can be provided along the interfaces of the adjacent components. Each of the components can match a corresponding anatomic portion in three dimensions and can be configured for surgical placement on the patient and can include a guiding formation that is related to an axis associated with the anatomic portion. Such axes can be tangential or perpendicular or at other specified angle relative to the anatomic portion and relative to various anatomic axes of the joint, such as, for example, the mechanical axis, the epicondylar axis or other anatomic axis.

Figure 7:
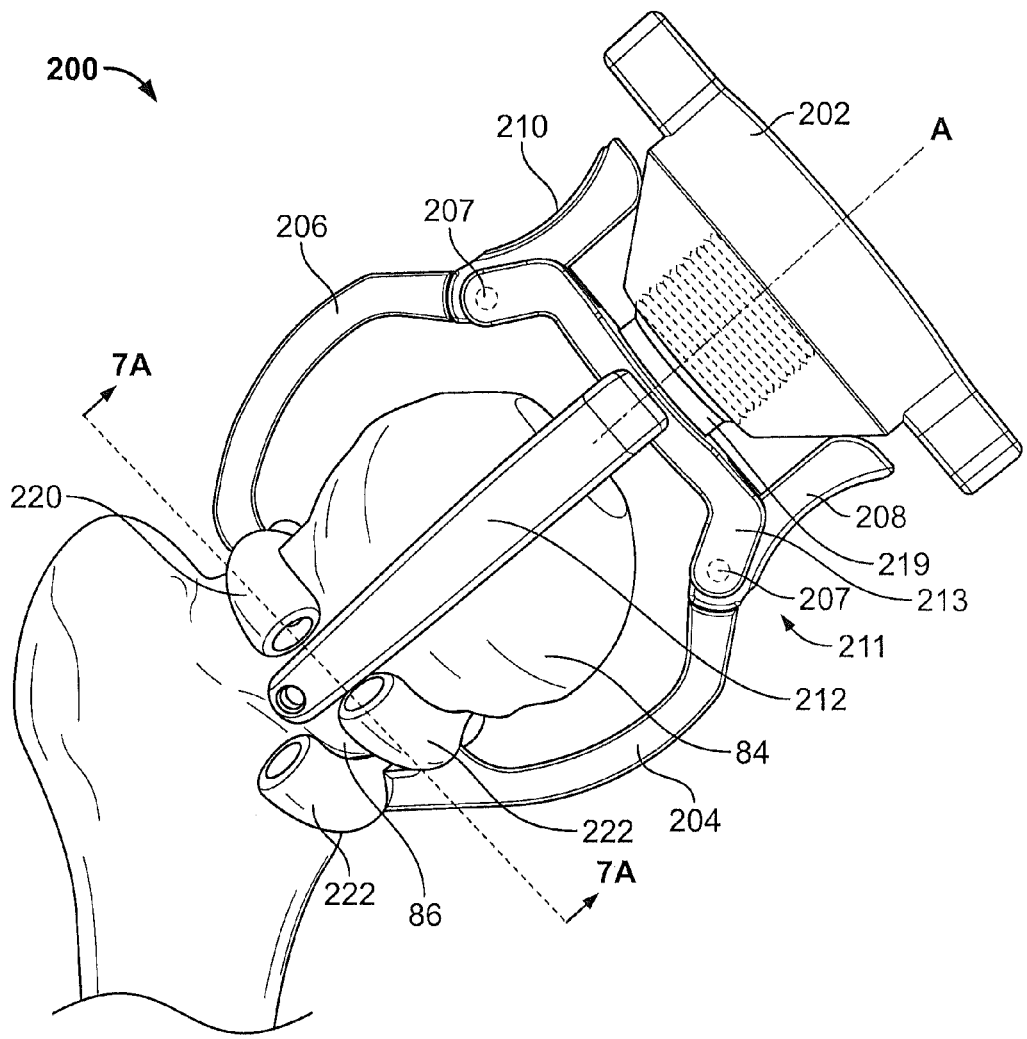
FIG. 7 is an environmental view of a patient-specific guide according to the present teachings.
Figure 8:
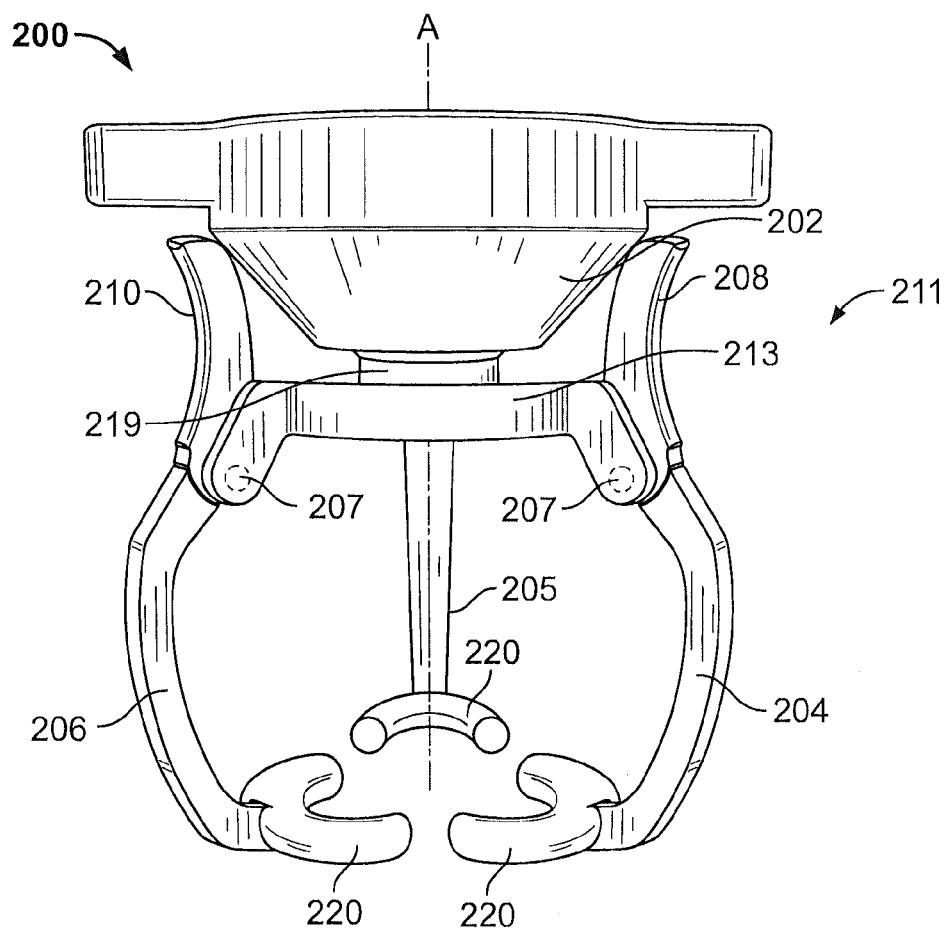
FIG. 8 is a perspective view of a patient-specific guide according to the present teachings.
Figure 8A:
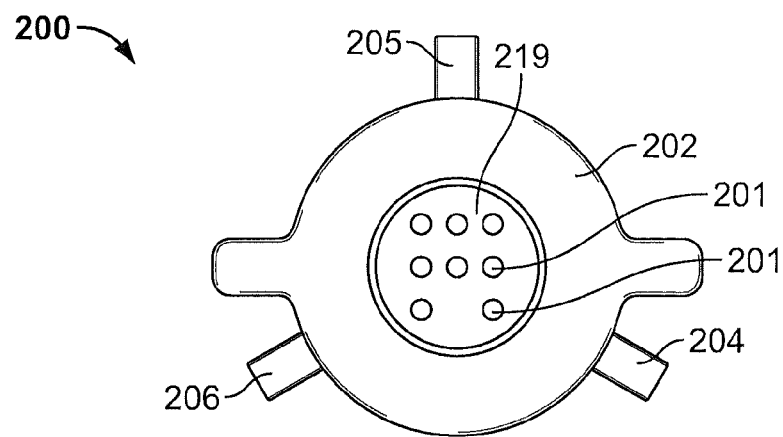
FIG. 8A is a plan view of patient-specific guide of FIG. 8.
Figure 9:
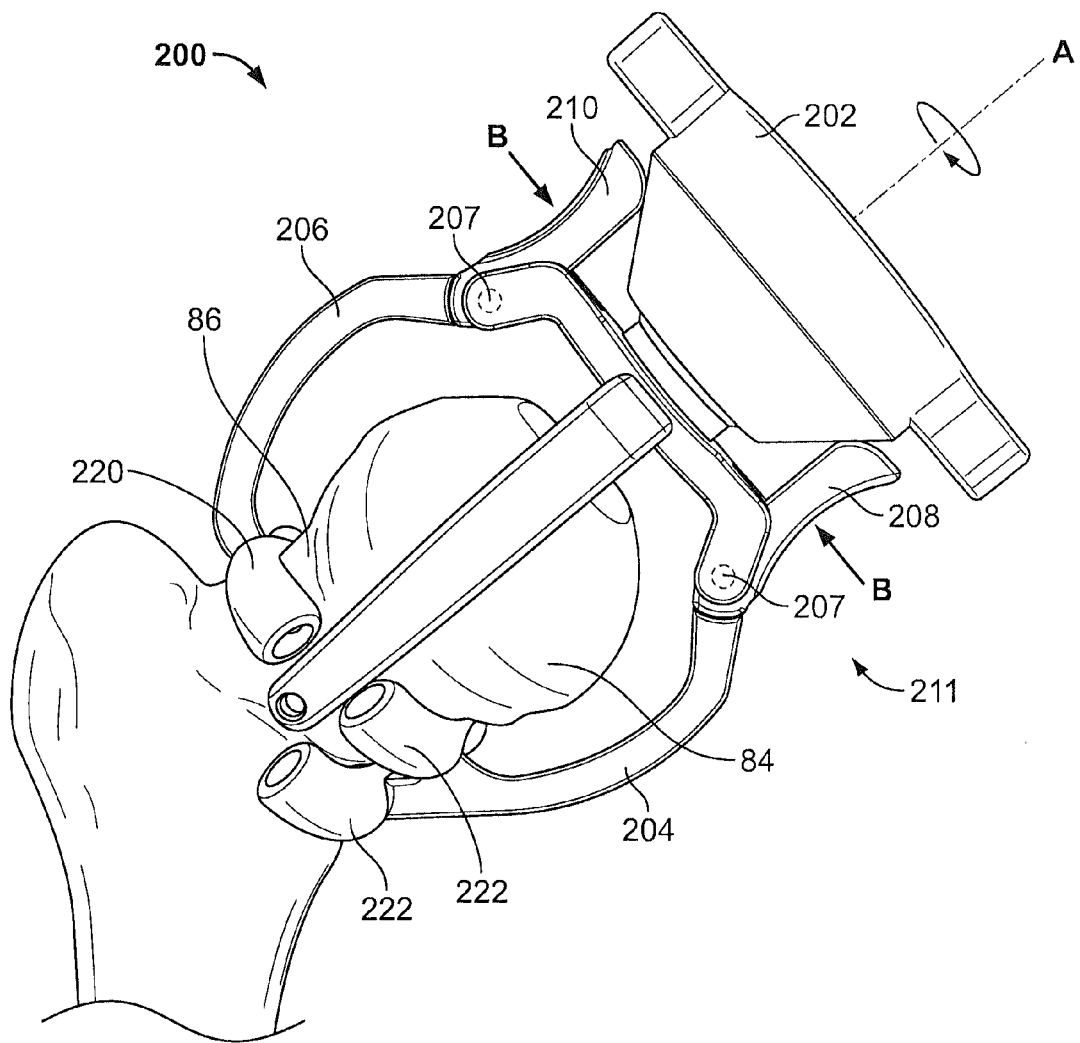
FIG. 9 is a perspective environmental view of a patient-specific guide according to the present teachings.

Referring to FIGS. 7-9, a patient-specific alignment guide 200 according to various embodiments is illustrated. The alignment guide 200 can include a frame 211 including a nut or other securing member 202, a body 213, a removable target member 212, and first and second arms 204, 206 movable between an open (non-engaging) and closed (engaging or clamping) configuration and pivotably coupled to the body 213 with pins or other pivots 207. The securing member 202 can be threadably connected to a threaded portion of a post 219 extending from the body 213. First and second tabs or extensions 208, 210 can extend from the corresponding first and second arms 204, 206 in the direction of the post 219. When the securing member 202 is fully threaded to the post 219, the securing member 202 pushes against the first and second extensions 208, 210 forcing and securing the first and second arms 204, 206 to the closed/clamping configuration around the patient's anatomy, as shown in FIG. 7. The post 219 can include a plurality of longitudinal passages 201 (shown in FIG. 8A) having different orientations relative to and converging toward a longitudinal axis A of the post 219, as shown in FIGS. 7, 8A and 9. The passages 201 can be arranged to form a tool guide and can be used for passing guide wires, fixation pins, drills or other tools. The first and second arms 204, 206 can include patient-specific clamping portions 220, 222, as described below.

The frame 211 (excluding the patient-specific portions discussed below) can be any instrument guiding frame for femoral resurfacing procedures, such as, for example, the RECAP® KS Alignment Device, commercially available from Biomet, Inc. of Warsaw, Ind. Further details of a related frame can be found in WIPO publication WO 2008/040961, the disclosure of which is incorporated herein by reference. Other embodiments of a frame 211 according to the present teachings are discussed below.

Figure 7A:
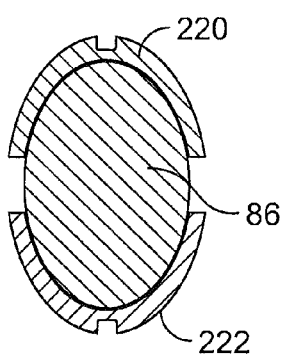
FIG. 7A is a sectional view of FIG. 7 taken along axis 7A.

Referring to FIGS. 7A and 7B, in various embodiments according to the present teachings, each clamping portion 220, 222 can be made to be patient-specific using the methods described above and can conform to the three-dimensional anatomy of the femoral neck 86 or a femoral head 84 of a specific patient, as shown in FIGS. 7A and 8E, for example. The clamping portions 220, 222 can be integral to the corresponding arms 206, 208 and made of the same material, such as a biocompatible metal. As illustrated in FIG. 7, the second arm 204 can include a pair of spaced-apart clamping portions 222 that are coupled to one another. It should be noted that one or both of the first and second arms 204, 206, can utilize this dual clamping configuration, Referring to FIGS. 7B and 7C, in various embodiments according to the present teachings, the first and second arms 204, 206 can be modular, such that the corresponding patient-specific clamping portions 220, 222 can be removably coupled to the first and second arms 204, 206. The modular connection can be a groove-and-tab connection, as illustrated in FIG. 7B, which shows an exemplary groove/slot 230 and tab 231 in arm 206 and a corresponding tab/extension/hook 233 and groove/slot 232 associated with clamping portion 220. The tab 231 can be received in slot 232 while the tab 233 can be received in slot 230. It will be appreciated that the relative locations of the groove and tab can be reversed. Different types of removable connections can be used, including snap-on, dovetail, or other quick-coupling and de-coupling connections. The modular clamping portions 220, 222 can be of single-use, while the frame 211 can be sterilizable and reusable. In various embodiments, the modular clamping portions 220, 222 can be non patient-specific and provided in different sizes and/or in a kit form. Different biocompatible materials can be used for the modular clamping portions 220, 222 and the frame 211, such as metallic materials for the frame 211 and plastic materials for the modular clamping portions 220, 222, although other materials biocompatible materials can also be used.

Referring to FIG. 7D the clamping portions 220, 222 can be generic metallic portions, which can be fitted with patient-specific clamping covers 240. Each patient-specific cover 240 can include a three-dimensional patient specific surface 242. The patient-specific surface can be constructed from three-dimensional image data of the patient, as described above, and can closely match or conform, for example as negative mold, to a corresponding surface of the specific patient's femoral anatomy, such as the femoral neck 86, as shown in FIG. 7A or the femoral head 84, as shown in FIG. 8E. The patient specific cover 240 can include a groove or slot or opening 244 for fitting the cover 240 onto the corresponding clamping portion 220, 222. The covers 240 can be made of a compliant, soft and flexible material, such as a plastic, for easy fitting onto the clamping portions 220, 222 and can be single use or disposable covers that can be used with a sterilizable and reusable frame 211, such as a metallic frame. The covers 240 can also be provided in different sizes for non patient-specific uses.

Referring to FIGS. 8-8D, the patient-specific alignment guide 200 can be provided with more than two arms, such as first, second and third arms 204, 206, 205 with corresponding clamping portions 220. The first, second and third arms 204, 206, 205 can be arranged circumferentially at 120 degrees apart relative to the body 113. The clamping portions 220 can be patient specific for direct and full contact with the three-dimensional anatomy of the femoral neck 86, as shown in FIGS. 8B and 8C, or the three-dimensional anatomy of the femoral head 84, as shown in FIG. 8E, correspondingly providing curved surface contact with the femoral neck or femoral head. The clamping portions 220 can be modular, snap-on patient-specific components, such as those illustrated in FIG. 7B, or can be provided patient-specific disposable covers 240, such as those illustrated in FIG. 7D. In various embodiments, the clamping portions 220 can include pointed tips 221 for point-contact at relative distances determined for a specific patient, as shown in FIG. 8C. Instead of point tips 221, line edges can be used for patient-specific line contact in three dimensions.

In various embodiments, and referring to FIG. 9, the various clamping portions 220, 222 and patient-specific covers described above can be selectively used with a frame 211 in which the first and second arms 204, 206 can be spring-loaded at the pivot pins 207 and biased in the closed or clamping position around the femoral neck 86 or femoral head 84. The first and second arms 204, 206 can be released from the clamping position by applying pressure on corresponding first and second extensions 208, 210 in the direction of the arrows B shown in FIG. 9.

The foregoing discussion discloses and describes merely exemplary arrangements of the present teachings. Furthermore, the mixing and matching of features, elements and/or functions between various embodiments is expressly contemplated herein, so that one of ordinary skill in the art would appreciate from this disclosure that features, elements and/or functions of one embodiment may be incorporated into another embodiment as appropriate, unless described otherwise above. Moreover, many modifications may be made to adapt a particular situation or material to the present teachings without departing from the essential scope thereof. One skilled in the art will readily recognize from such discussion, and from the accompanying drawings, that various changes, modifications and variations can be made therein without departing from the spirit and scope of the present teachings.

What is claimed is:

1. An orthopedic apparatus comprising:
    an alignment guide attachable to a femoral head and a femoral neck portion of a femur of a specific patient, the alignment guide including first and second members coupled with corresponding first and second connecting portions and forming a complete shell for encompassing the femoral head, the alignment guide having a patient-specific three-dimensional bone engagement surface constructed from a three dimensional image of the femoral head surface and femoral neck surface obtained from medical imaging of the femoral joint surface of the specific patient, the engagement surface including a substantially concave portion and configured to closely conform and matingly contact as a negative mold of the femoral head surface, the engagement surface including a substantially convex portion configured to closely conform and mate as a negative mold of the femoral neck surface of the specific patient, the alignment guide including at least one guiding portion defining a guiding passage.

2. The orthopedic apparatus of claim 1, wherein the patient specific engagement surface includes portions oriented along first and second substantially orthogonal planes of the femoral joint.

3. The orthopedic device of claim 1, wherein the first and second connecting portions form a tongue and groove connection.

4. The orthopedic device of claim 1, wherein the first and second members are flexible.

5. The orthopedic device of claim 1, wherein the first and second connecting portions form a snap-on connection.

6. An orthopedic apparatus comprising an alignment guide attachable to a femoral joint surface of a femur of a patient, the alignment guide having a patient-specific three-dimensional engagement surface configured to closely conform and matingly contact as a negative surface of a corresponding surface of a femoral head and femoral neck of the femoral joint surface, the alignment guide shaped as a complete shell for encompassing the femoral head and including:
   first and second members configured to completely surround and encompass and matingly contact the femoral head of the femoral joint surface, wherein the first and second members are patient-specific, curved and substantially concave toward the femoral head;
   first and second connecting portions coupled to the first and second members and configured to contact and surround and encompass the femoral neck of the femoral joint surface, wherein the first and second connecting portions are patient specific and convex toward the femoral neck and are connected to one another with a releasable connection; and
   a longitudinal guiding portion extending perpendicularly from the shell and defining a guiding passage configured to receive a tool.

7. The orthopedic device of claim 6, wherein the releasable connection is a tongue and groove connection.

8. The orthopedic device of claim 6, wherein the first and second members are flexible.

9. The orthopedic device of claim 6, wherein the releasable connection is a snap-on connection.

* * * * *

UNITED STATES PATENT AND TRADEMARK OFFICE
CERTIFICATE OF CORRECTION

PATENT NO. : 8,858,561 B2  
APPLICATION NO. : 12/486992  
DATED : October 14, 2014  
INVENTOR(S) : John R. White et al.

Page 1 of 1

It is certified that error appears in the above-identified patent and that said Letters Patent is hereby corrected as shown below:

On the Title Page

Column 1, item (73) Line 1; Delete "Blomet" and insert --Biomet--.

Column 1, item (56) Line 2; Delete "Arthuroplasty," and insert --Arthroplasty,--.

Column 2, item (56) Line 33; Delete "Hazen," and insert --Hazan,--.

In the Specification

Column 5, Line 37; Delete "neck." and insert --neck--.

Column 6, Line 38; Before "head", insert --femoral--.

Column 6, Line 63; Before "alignment", insert --patient-specific--.

Signed and Sealed this  
Seventh Day of April, 2015

Michelle K. Lee  
*Director of the United States Patent and Trademark Office*